(12) United States Patent
Das et al.

(10) Patent No.: US 6,316,197 B1
(45) Date of Patent: Nov. 13, 2001

(54) METHOD OF DIAGNOSING OF EXPOSURE TO TOXIC AGENTS BY MEASURING DISTINCT PATTERN IN THE LEVELS OF EXPRESSION OF SPECIFIC GENES

(75) Inventors: Rina Das, Rockville, MD (US); Marti Jett, Washington, DC (US); Chanaka Mendis, Falls Church, VA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/495,724

(22) Filed: Feb. 1, 2000

Related U.S. Application Data

(60) Provisional application No. 60/118,776, filed on Feb. 5, 1999.

(51) Int. Cl.[7] ............................. C12Q 1/68; C12P 19/34; C07H 21/04

(52) U.S. Cl. ........................... 435/6; 435/91.2; 435/91.5; 536/24.31

(58) Field of Search ................................. 435/6, 7.1, 325, 435/375, 91.2, 91.5; 436/536; 514/44; 536/24.31

(56) References Cited

FOREIGN PATENT DOCUMENTS

| WO/94/26307 | 11/1994 | (WO) | ............................ A61K/39/295 |
| WO/97/02756 | 4/1997 | (WO) | ............................... C12Q/1/68 |

OTHER PUBLICATIONS

Mendis, "Identification of alterations in gene expression in response to staphylococus enterotoxin B (SEB) using differential display (DD)", Molecular Biology of the Cell, vol. 9, No. Sup, 1998, p. 450A, Abstract.

Pomerantsev, "Expression of cereolysine AB genes in Bacillus anthracis vaccine strain ensures protection against experimental hemolytic anthrax infection", Vaccine, GB, Butterworth Scientific., Guildford, vol. 15, No. 17–18, Dec. 1, 1997, pp. 1846–1850, abstract.

Ledakis et al. "limitations of Differential Display", Biochemical and Biophysical Research Communications vol. 251, pp. 653–656, Oct. 1998.*

* cited by examiner

Primary Examiner—Robert A. Schwartzman
Assistant Examiner—Karen A Lacourciere
(74) Attorney, Agent, or Firm—Elizabeth Arwine

(57) ABSTRACT

A method of diagnosing exposure to a toxic agent comprising the steps of detecting the amount of protein/gene expression present in a sample of mammalian tissue or mammalian body fluids that has not been exposed to a toxic agent. Then the amount of protein/gene expression present in a sample of mammalian tissue or mammalian body fluids that has been exposed to the toxic agent is detected. A determination of the difference in the detected amount of protein/gene expression between the exposed and unexposed samples is made. A comparison of the difference to a library of expected protein/gene expression for predetermined toxic agents is made. Finally, an evaluation is made whether the difference indicates the exposure to a particular toxic agent. A treatment method for administering a therapeutic agent which inhibits the mechanistic pathways necessary to maintain the progression of lethal shock is also disclosed.

20 Claims, 27 Drawing Sheets

Time dependent expression of CTAP-III through RT-PCR

Time dependent expression of proteoglycan VI

Time dependent expression of GBP

Time dependent expression of HIF-1

Time dependent expression of IL-6

Time dependent expression of Ferritin heavy chain

Expression of IL6 in response to SEB in monkey samples

Expression of GBP in response to SEB in monkey samples

Comparison of expression of a cDNA, which codes for HIF-1. Equal

Expression pattern of RhoE in human kidney cells in response to SEB

Differential expression pattern of Interleukin-6 in human kidney cells in response to SEB Differential expression pattern of Interleukin-6 in human kidney cells in response to LPS Expression pattern of Ferretin heavy chain in human kidney cells in response to LPS Comparison of Ferritin gene expression in human kidney cells in response to LPS and SEB Comparison of GBP gene expression in human kidney cells in response to LPS and SEB Comparison of Myosin heavy chain gene expression in human kidney cells in response to LPS and SEB Comparison of HIF-1 gene expression in human kidney cells in response to LPS and SEB Effect of p-38 in SEB induced cell proliferation Effect of p-38 on TNF-alpha induction Effect of -p-38 inhibitor on CD-69 expression SEB-Induced Proliferation: Inhibition by HPA-Na Inhibition of SEB-Induced Proliferation:
Protein kinase C inhibitors SEB-Induced TNF-α Production: Effects of PKC Inhibitors

Fig. 28

Expression of Ferretin heavy chain in response to Anthrax

Fig. 29

Expression of HIF-1 after Anthrax exposure

Fig. 30

Expression of GBP in Anthrax treated cells (Bar chart: Relative Units vs Time (hrs))
- 0 hrs: ~0.67
- 2 hrs: ~0.45
- 8 hrs: ~0.54
- 12 hrs: ~0.55
- 24 hrs: ~0.51

Fig. 31

Expression of IL6 after Anthrax exposure in human lymphoid cells (Bar chart: Relative Units vs Time (hrs))
- 0 hrs: ~0.41
- 2 hrs: ~0.50
- 8 hrs: ~0.41
- 12 hrs: ~0.65
- 24 hrs: ~0.83

Fig. 32

Expression of ILT6 in Anthrax treated cells (Bar chart: PERCENT CONTROL vs CONTROL, Anth 6, Anth 12)

Fig. 33a

Expression of Cathepsin L in Anthrax treated cells (Bar chart: PERCENT CONTROL vs CONTROL, Anth 6, Anth 12)

Fig. 33b

Changes in gene expression in human peripheral blood lymphoid cells in response to Anthrax

Fig. 34

Changes in expression of GBP in response to SEB vs Anthrax

Changes in expression of IL-6 in response to
SEB vs Anthrax

Changes in expression of HIF-1 in response to
SEB vs Anthrax

Fig. 38

DD-PCR analysis of cells
exposed to Anthrax

AP1   AP    AP2   AP1   AP2

ARP1  ARP   ARP1  ARP3  ARP1

Fig. 39

DD-PCR analysis of human peripheral
blood lymphoid cells exposed to Yersinia Pestis (Plague)

| AP1 | AP3 | AP1 |
| ARP1 | ARP2 | ARP2 |
| Plague Control | Plague Control | Plague Control |

DD-PCR analysis to show lymphoid cell responses to Cholera Toxin

AP2  ARP2, Gel 11/16/99

Up-regulation in Cholera

1 = Control
2,3 = Cholera 2 hr.
4,5 = Cholera 16 hrs.
6 = SEB

Comparison of changes in gene expression in response to SEB and Cholera Toxin

Fig. 41

Expression of GBP in peripheral blood lymphoid cells of monkeys challenged with SEB

METHOD OF DIAGNOSING OF EXPOSURE TO TOXIC AGENTS BY MEASURING DISTINCT PATTERN IN THE LEVELS OF EXPRESSION OF SPECIFIC GENES

This application claims the benefit of priority of application Ser. No. 60/118,776, filed on Feb. 5, 1999.

FIELD OF THE INVENTION

The present invention relates to a novel method of diagnosing the exposure of a subject to toxic agents based on relative ratios, amounts or changes in levels of the genes/proteins in mammalian tissue or body fluids from normal levels. The present invention further relates to compositions, and uses thereof, for treating lethal shock induced by toxic agents.

BACKGROUND OF THE INVENTION

The threat of terrorist action using biological warfare (BW), chemical or infectious agents has occurred throughout the world. These acts of terrorism are unpredictable and counter efforts have been aimed at rapid, accurate diagnosis and speedy treatment. Determination of the exact toxin that a subject has been exposed to is critical to treatment. More over, immediate determination of the exact toxin exposure is necessary to prevent irreparable damage, incapacity and death.

Current methods for pathogen or toxin identification require specialized reagents that are structural-based probes. For bio-engineered toxic agents, those probes may prove to be ineffective. The increased sophistication available for design of potential biological weapons will require reliance on better approaches to adequately identify such threats. Simple identification of toxins or infectious agents may be complicated by the fact that genetic manipulations could (1) make BW agents unrecognizable by structural-based technologies, or (2) enhance their devastating effects, making them toxic at undetectable levels. Furthermore, small amounts of common bacterial products, such as protein A or endotoxin, have been shown to markedly potentate activities of biological warfare threat toxins. The difficulties of identifying toxins experienced in the past could lead to potentially disastrous delays in responding appropriately to the threat or to the possibility of inappropriate treatment based on inadequate information. Thus far, diagnoses could only be made based on symptcoms, which may take 4–24 hours or more to appear, and by that time, the damage is irreversible and death may result.

Description of a Selected Group of Toxic Agents:

There are many toxic agents that are a threat to humans in situations of biological warfare. For example, SEB: Staphyloccocal enterotoxin B is a potent bacterial toxin known to cause lethal shock. The mode of exposure could be aerosol, food or water contamination. It interacts with the lymphoid cells, proximal tubule (PT) kidney and other cells initiating cascades of reactions ultimately leading to lethal shock. The initial symptoms for SEB-induced intoxication are vertigo, muscle weakness (vasoconstriction in the extremities) within 1–8 hrs of exposure to the toxin. The symptoms that follow are nausea, vomiting and diarrhea, along with hypotension and vasodilation of blood vessels in kidney and other organs (1–24 h). Respiratory distress and pathological hypotension eventually lead to irreversible shock and death at about 40–60 hrs post exposure, although very early incidents (ca. 6 h) have been observed. The mechanism of its action is not clear, nor is it understood how SEB is massively potententated by trace levels of contaminants such as Protein A or endotoxin. In short, there is no system available to determine host exposure or individual responses and the toxin is rapidly (30 min) removed from the blood stream to the kidney PT (75%), liver and spleen.

Anthrax is another highly toxic agent. Anthrax is a natural disease of herbivorous animals that can be transmitted to humans. The causative agent *Bacillus anthracis*, can form spores which are extremely hardy and can remain alive for a very long time. After inhalation of a heavy dose of anthrax spores, however, the onset of the disease may occur within a day and death may follow rapidly in a couple of days. The molecular changes caused by this agent in the host is totally unknown, therefore identifying genes altered by this agent is very crucial for rapid and effective detection.

Brucella is a highly infectious bacteria that causes disabling syrnptomatology (fever, chills, fatigue) in humans. Bacteria can be acquired through inhalation, ingestion, or penetration of damaged skin. As facultative intracellular parasites of macrophages, they primarily localize in the reticuloendothelial system. Bacteremia and symptoms occur from several days to several weeks after infection, presumably as a result of amplification of bacterial numbers in spleen, liver and bone marrow. Host response involves both Th1 and Th2 immune mechanisms, but is generally tilted toward Th1. In murine models of brucellosis, both antibody and T cells transfer immunity. Brucella LPS is relatively nonpyrogenic compared to LPS fiom Enterobacteriaceae. This property may explain the relative paucity of immune and inflammatory response early in infection Plague is still another threatening toxic agent to man. The *Y. pestis* is an organism that causes plague. Plague symptoms include fever, chills, headache, hemoplysis and toxemia. This eventually leads to respiratory failure and death. Until now, diagnosis has been made by symptom analysis. This means that the progress of the illness can go unchecked before treatment is sought and is therefore, unsuccessful. A faster test is needed for plague.

Botulinum toxin is extremely potent neurotoxins produced by different strains of the bacterium *Clostridium botulinum*. There are seven serotypes of botulinum toxins, which share the same functional mechanism: they have an endopeptidase activity that cleaves a protein in synaptic vesicles thereby inhibiting release of acetycholine. The resulting block in neurotransmitter release causes general skeletal muscle paralysis with death occurring due to respiratory failure. Following inhalation or ingestion of botulinum toxin, symptoms may appear within 24 to 36 hours or may take several days to appear. This toxin causes weakness, dizziness, dry mouth and throat, blurred vision and diplopia, dysarthria, disphonia, dysphasia and respiratory failure. A faster test for exposure to the botulinum toxin is needed.

Cholera Toxin (CT) causes vomiting, headache, diarrhea resulting in death. Mortality is as high as 80%. Diagnosis is done by symptoms of diarrhea and dehydration. The Cholera Toxin is a very difficult toxin to spot in a blood sample. Therefore, a faster, non-symptom related test is needed to prevent death.

There is no easy or fast detection method to confirm the exposure to these and other toxic agents. The deadly symptoms of lethal shock appear before they are diagnosed so the important life-saving treatment is delayed which results in deaths that could be prevented if an earlier test were available. Current methods for pathogen identification using structural-based probes may not be useful for early diagnosis for the reasons stated above.

Therefore, an object of the present invention is to provide for a method of diagnosing exposure to toxic agents by measuring distinct patterns in the levels of expression of specific genes.

Another object is to provide a library of host gene expression responses to toxins such as anthrax, botulinum, Brucella, plague and cholera in comparison with altered gene expression in response to the staphylococcal enterotoxins and lipopolysaccharide (SEB).

It is a further object of the invention to select a panel of genes, the altered pattern of expression of which will provide a fingerprint that is indicative of exposure to a particular toxic agent, has the potential to reveal the severity of exposure and the individual susceptibility to the agent, and can provide indicators of course of impending illness for even unknown toxic agents.

A still further object of the invention is to utilize peripheral blood lymphoid cells from exposed individuals since these cells are a readily accessible reservoirs of historical information and they show unique patterns of responses although they may not be the primary target of a toxin.

A further object of the invention is to determine host functional responses to toxic agent exposure prior to onset of symptoms or illness.

A still further object of the invention is to provide a method of early treatment of subjects exposed to toxins with the intervention of drugs or with agents, such as antisense codes, which turn off the expression of genes that react detrimentally to toxins, based on the newly found gene changes.

SUMMARY OF THE INVENTION

With the method of the present invention, the problems experienced in the past are solved. With the present invention both known and presently unknown or bio-engineered biological warfare (BW) agents can be identified based on early host functional responses to exposure. The present method also has the benefit of revealing she presence of low-level potentiating contaminants, such as LPS and Protein A which cause the toxins to have a more potent effect on an exposed subject. The present invention provides early information regarding individual exposure and susceptibility. This approach offers the benefits of immediate diagnosis, and the ability to identify those who have been exposed to toxic agents but have not yet developed signs or symptoms.

The present invention solves the problems of the past with a method whereby an individual's exposure and his/her response to a toxic agent based on alterations in gene expression in their peripheral blood lymphoid cells can be determined. These cells are readily available from personnel. These cells serve as a reservoir of historical information; although they may not, themselves, be the pathogenic target of a toxic agent, the toxic agents can indirectly activate lymphoid cells to produce a unique gene expression patterns typical of the impending illness. In addition to diagnostics, the gene expression profile potentially provides a regimen for specially designed, appropriate treatment.

The present invention is, thus, directed to a method of diagnosing exposure to a toxic agent comprising the steps of detecting the amount of protein/gene expression present in a sample of mammalian tissue or mammalian body fluids that has not been exposed to a toxic agent. Then the amount of protein/gene expression present in a sample of mammalian tissue or mammalian body fluids that has been exposed to the toxic agent is detected. A determination of the difference in the detected amount of protein/gene expression between the exposed and unexposed samples is made. A comparison of the difference to a library of expected protein/gene expression for predetermined toxic agents is made. Finally, an evaluation is made whether the difference indicates the exposure to a particular toxic agent. The present invention is particularly useful because it can provide a diagnosis of whether a person has been exposed to a toxic agent before the onslaught of any symptoms.

The present invention is also directed to a method of diagnosing exposure to a toxic agent comprising the steps of detecting the patterns of gene expression/proteins present in a sample of mammalian tissue or mammalian body fluids from persons that have been exposed to potentially toxic agent(s), determining the relative amounts of expression of a panel of genes relative to house keeping genes expressed in those tissues from the potentially exposed individuals, comparing the relative amount differences to a library of expected gene expression/proteins for predetermined toxic agents; and evaluating whether the differences indicate that exposure has occurred to a known, catalogued, toxic agent, to a previously unknown toxic agent, or to a toxic agent mixed with potentiating agents. Housekeeping genes are genes that tend not to change upon exposure to toxic agents.

BRIEF DESCRIPTION OF THE FIGURES

FIG. 28 is a graph showing expression of Ferretin heavy chain in response to Anthrax;

FIG. 29 is a graph showing expression of HIF-1 after Anthrax exposure;

FIG. 30 is a graph showing expression of GBP in Anthrax treated cells;

FIG. 31 is a graph of expression of IL-6 after Anthrax exposure in human lymphoid cells;

FIG. 32 is a graph of expression of ILT6 in Anthrax treated cells;

FIG. 33a is a graph of expression of cathepsin L in Anthrax treated cells;

FIG. 33b is a graph of expression of HCI and EIF3 upon exposure to Anthrax;

FIG. 34 is a graph of the changes in expression of a GBP in response to SEB vs Anthrax;

FIG. 38 is a digital differential display gel profile showing gene profiles of SEB exposed sample and Anthrax exposed samples as compared to gene profiles of a control;

FIG. 39 is a digital differential display gel profile showing gene profiles of plague exposed samples as compared to gene profiles of a control;

FIG. 41 is a graph showing the expression of GBP in peripheral blood lymphoid cells of monkeys challenged with SEB.

DETAILED DESCRIPTION

Discussion of the Figures and Tables

Effect of SEB on the Expression of Different Genes:

RT-PCR was performed on RNA samples from human lymphoid cells treated with SEB for different time periods. Several changes in expression of genes were observed that were up regulated or down regulated in response to the toxin in a time dependent manner as summarized in Table 1.

Figure 1:
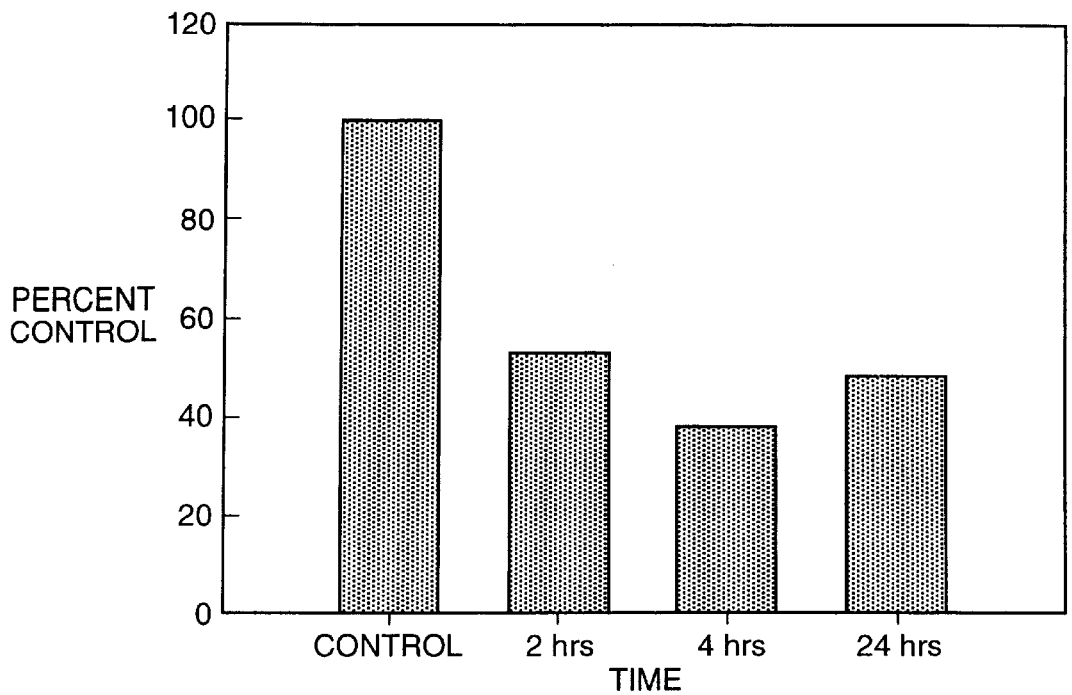
FIG. 1 is a graph showing a time dependent expression of CTAP-III through RT-PCR wherein the levels of the CTAP-III gene go down upon SEB exposure.
Figure 2:
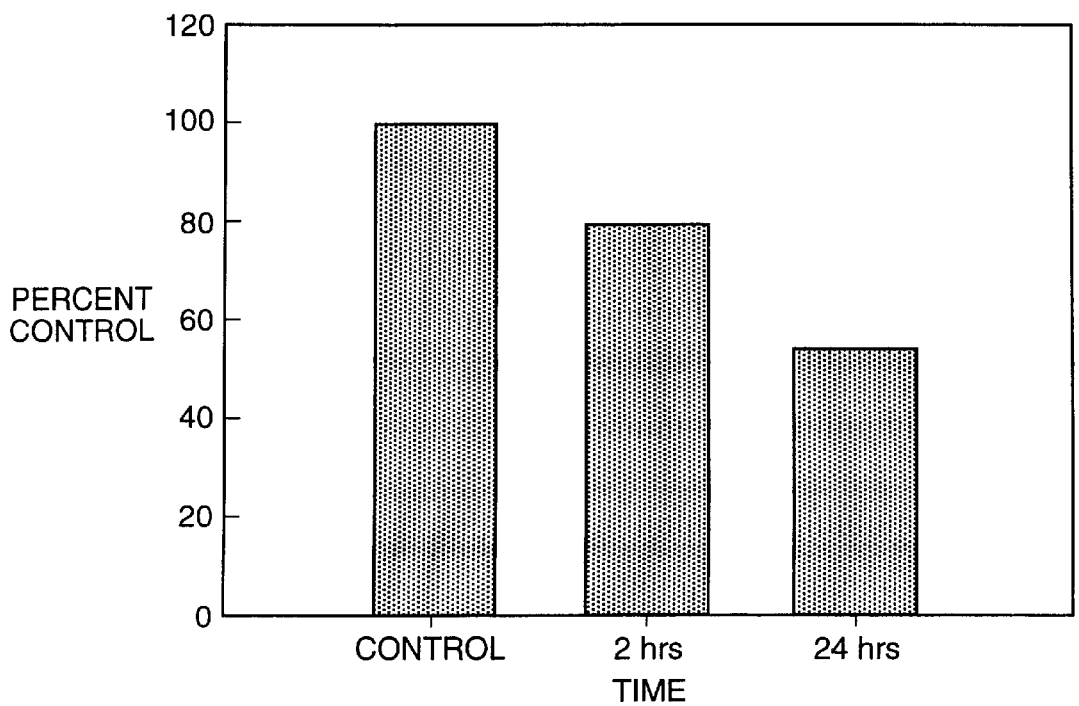
FIG. 2 is a graph showing a time dependent expression of proteoglycan V1.
Figure 10:
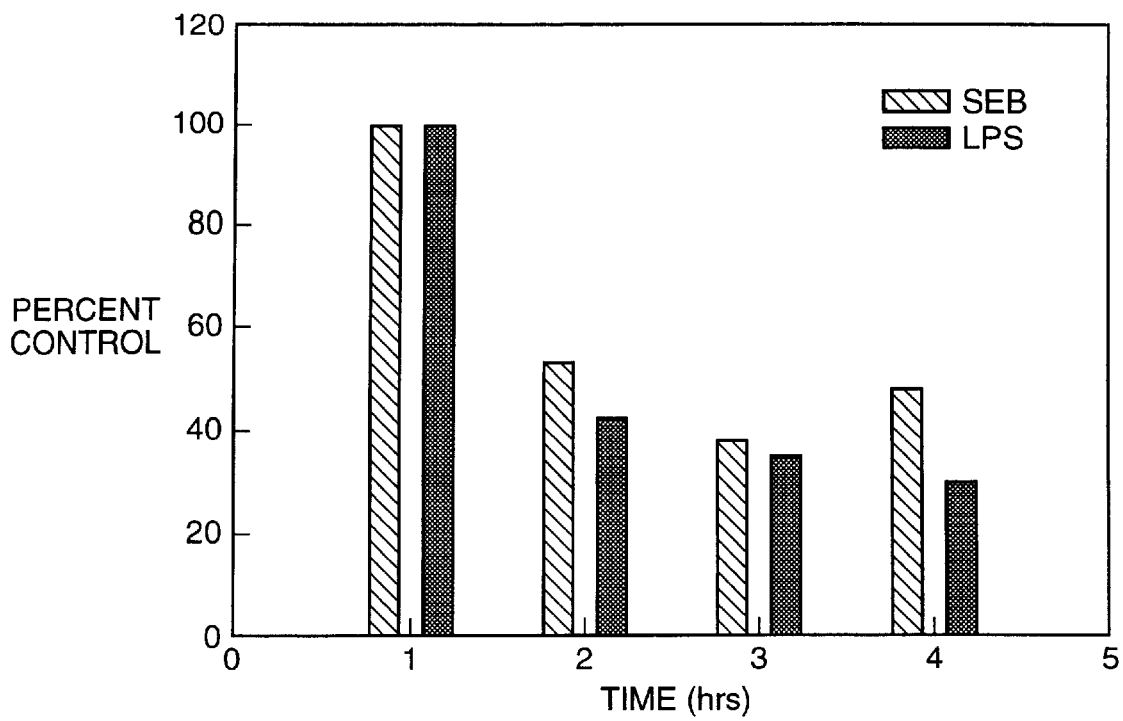
FIG. 10 is a graph showing a comparison of expression of a cDNA, which codes for CTAP-III induced by SEB or LPS.

Effect of SEB on the Expression of CTAP-III Gene:

The CTAP III gene was identified to be down regulated by SEB, which was confirmed by RT-PCR, and by Northern blot analysis. FIG. 1 shows the levels of CTAP-III going down upon SEB exposure. A down regulation of the expression of CTAP III was observed as early as 2 hours (40–60%), and this activity was retained even at 24 hours (40–60%).

Effect of SEB on the Expression of Proteoglycan Gene:

Primers were designed for proteoglycan $V_1$ (Vimentin) gene and RT-PCR performed on RNA samples from different time periods of SEB exposure. There was a dramatic decrease in expression upon SEB exposure (FIG. 2). Within 2 hrs the expression of this gene was down regulated to 70–85% of control levels and the expression levels were further decreased to 45–60% by 24 hours.

Effect of SEB on Gene Expression of GBP:

SEB exposure caused a significant increase in expression of this gene that is involved in Guanylate cyclase regulation (FIG. 3). A clear induction of the expression of GBP was evident as early as 2 hours (7.5–8 fold). Even though its activity gradually decreased by 24 hours, the levels were still well over control levels (3–3.5 fold).

Effect of SEB on Gene Expression of Hypoxia Inducible Factor (HIF-1):

The expression of the gene HIF-1 was also up regulated in response to SEB in a time dependant manner (FIG. 4). Increase of the expression of this gene was observed at 2 hrs (2–2.5 fold), and the expression continued to increase even at 24 hrs (2.5–3 fold).

Effect of SEB on Gene Expression of IL6:

IL6 gene expression was significantly up regulated upon SEB exposure within 2 hrs of exposure (FIG. 5). A significant enhancement of the expression of IL-6 was detected as early as 2 hrs (50–55 fold), and this enhanced expression was evident around 24 hours (30–35 fold).

Effect of SEB Exposure on Gene Expression of Ferritin Heavy Chain:

SEB exposure caused a decrease in the expression of Human Ferritin gene as shown in FIG. 6 by 24 hours. Even though ferritin expression was about 1.4–1.5 fold by 2 hrs, it gradually decreased by 24 hrs reaching 70–80% of control levels.

Confirmnation of Gene Changes in Monkey Blood Samples Exposed to SEB:

We verified these findings in lymphocytes of monkeys challenged with SEB. Using PCR primers designed for the selected genes, we have found unique patterns in alteration of gene expression as early as 30 minutes post-aerosol challenge. We tested three genes in lymphocytes from monkey blood samples after exposure to SEB (FIGS. 7–9).

The expression of IL6 and GBP was up regulated by 30 minutes of SEB challenge in monkey samples. This was a sub-lethal dose given to the monkeys so the expression of CTAP-III was also shown to be up regulated in these samples by 30 minutes of exposure. Similar results were obtained with human cells in vitro when exposed to SEB.

Summary of Changes: Table 2 summarizes all the changes that were observed that were induced by these toxins in human lymphoid cells.

Comparison of the Effects of SEB and LPS on Expression of CTAP-III

Equal amount of the RNA samples treated with SEB and LPS along with proper controls were reverse transcribed as described elsewhere and amplified using custom designed primers of CTAP-III. Equal volumes of samples were resolved on a 1% agarose gel, visualized by ethidium bromide staining and quantitated by NIH image program 1.61. #1, Control; #2–4 were treated with 100 ng/ml SEB or LPS for different time periods and were normalized with expression of β-actin. #2; 2 hrs, #3, 4 hrs; #4, 24 hrs. Both SEB and LPS toxins were capable of down regulating the CTAP-III gene while showing a similar activation pattern. Effect of LPS was prominent compared to SEB. Down regulation of the CTAP III gene was visible as early as 2 hrs (SEB 50% of control levels and LPS 45% of control levels). After 24 hrs of treatment expression of the CTAP-III gene induced by SEB was about 33–45% of control levels while LPS was 25–35% (FIG. 10). In FIG. 10, for each pair of results shown comparing SEB to LPS, the left band is SEB and the right band is LPS.

Comparison of the Effect of SEB and LPS on the Expression of the IL-6 GENE

Figure 11:
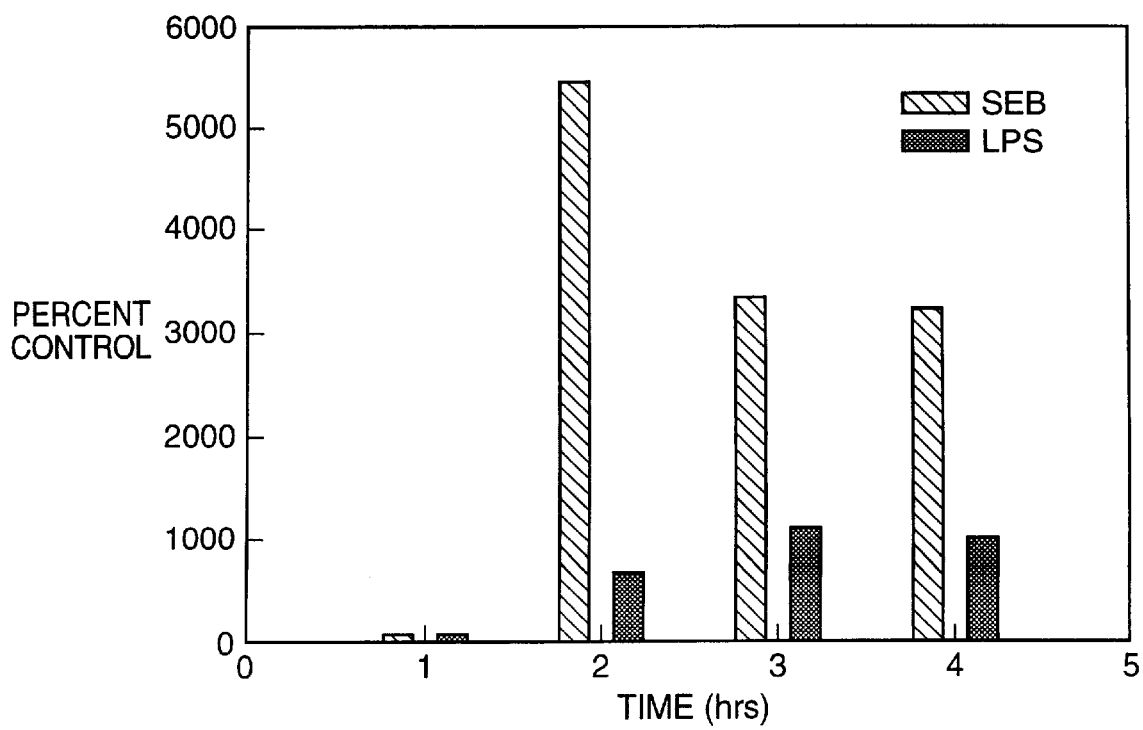
FIG. 11 is a graph showing a comparison of expression of IL-6 induced by SEB and LPS.

Equal amount of the RNA samples treated with SEB and LPS along with proper controls were reverse-transcribed as described elsewhere and amplified using custom designed primers of IL-6. Equal volumes of samples were run on 1% agarose gel in a gel loading buffer, subjected to electrophoresis at 100V for 40 min., visualized by ethidium bromide staining and quantitated by the NIH image program 1.61. #1, Control; #2–4 were treated with 100 ng/ml SEB or LPS for different time periods and were normalized with β-actin. #2; 2 hrs, #3, 4 hrs; #4, 24 hrs. Both toxins up regulated the expression of the IL-6 gene in a time dependent manner while the effect of SEB in human lymphoid cells was more prominent. An up regulation was seen as early as 2 hrs by both toxins (SEB 52–57 fold, LPS 7–8 fold), and was still up regulated at 24 hrs (SEB 30–35 fold, LPS 10–12 fold). SEB had a pronounced effect on IL-6 gene expression but with LPS it was not very significant (FIG. 11). In FIG. 11, for each pair of results shown comparing SEB to LPS, the left band is SEB and the right band is LPS.

Comparison of the Effects of SEB and LPS on Expression of GBP-2

Figure 12:
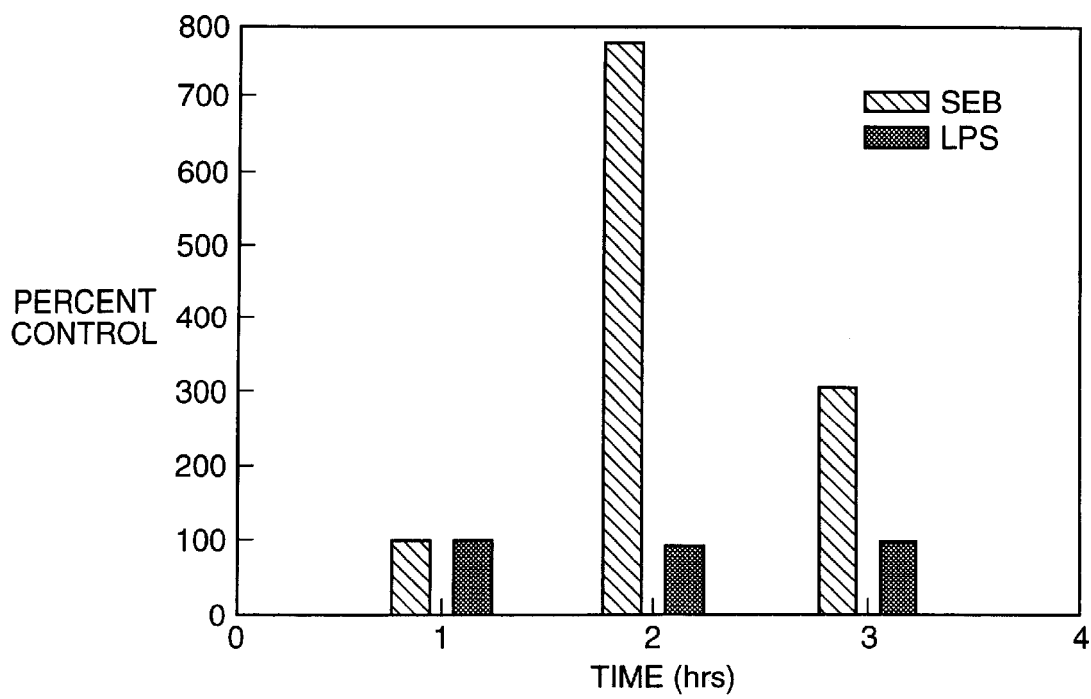
FIG. 12 is a graph showing a comparison of expression of a cDNA, which codes for GBP-2.

Equal amount of the RNA samples treated with SEB and LPS along with proper controls were reverse-transcribed as described elsewhere and amplified using custom designed primers of GBP-2. Equal volumes of samples were resolved on a 1% agarose gel, visualized by ethidium bromide staining and quantitated by the NIH image program 1.61. #1, Control; #2–3 were treated with 100 ng/ml SEB or LPS for different time periods and were normalized with β-actin. #2; 2 hrs, #3, 24 hrs. GBP was clearly up regulated by SEB by 2 hrs (7–8 fold), and was seen even after 24 hrs (3–3.5 fold). LPS had no effect on the expression of GBP-2 (FIG. 12). ). In FIG. 12, for each pair of results shown comparing SEB to LPS, the left band is SEB and the right band is LPS.

Comparison of the Effects of SEB and LPS on Expression of HIF-1

Figure 13:
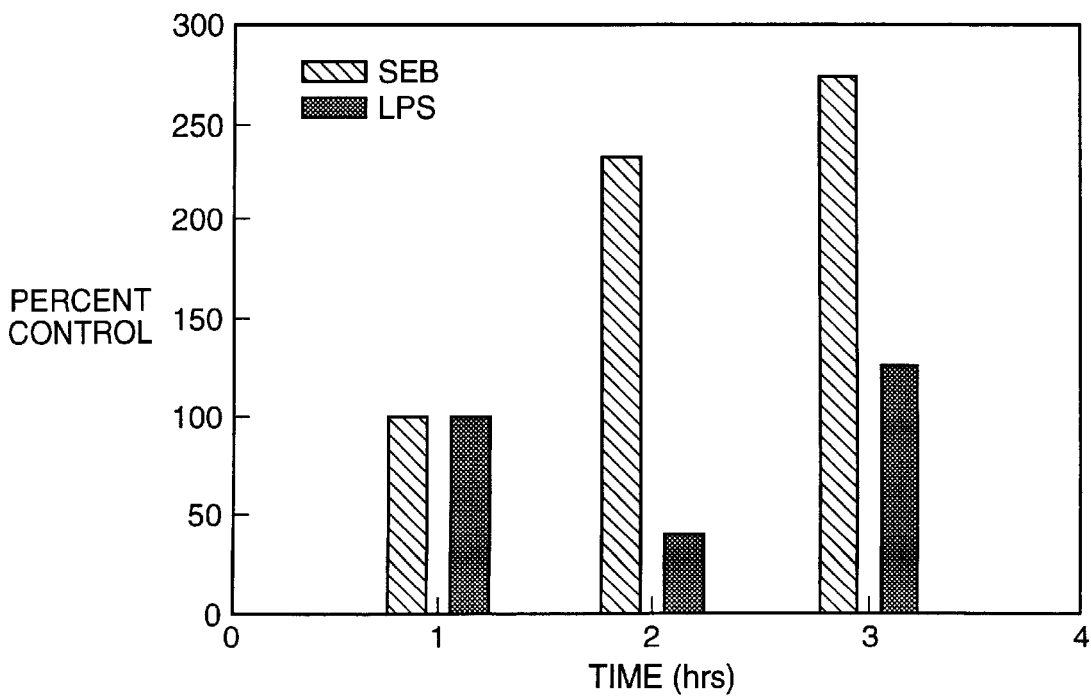
FIG. 13 is a graph showing a comparison of expression of a cDNA, wLich codes for HIF-1.

The HIF-1 gene expression was up regulated by SEB in a time dependent manner reaching an optimum value by 24 hrs (2.5–3 fold). Expression pattern of the HIF-1 gene by LPS was different to that observed for SEB. There was no significant change observed even after 24 hrs (FIG. 13). In FIG. 13, for each pair of results shown comparing SEB to LPS, the left band is SEB and the right band is LPS.

Summary of unique changes induced by SEB and LPS:
Table 3 summarizes the changes induced by SEB and LPS. The time dependent changes are also noted in this table.

Differential Gene Expression Patterns in Human Kidney Cells Induced by SEB

Figure 14:
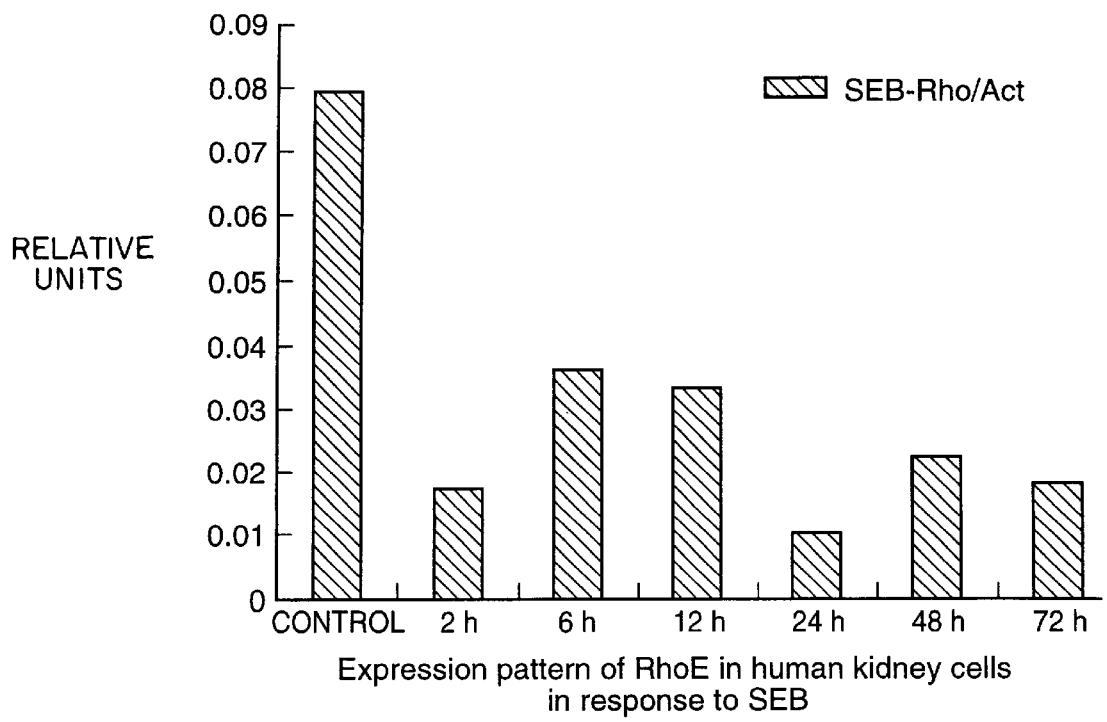
FIG. 14 is a graph showing expression pattern of RhoE in Human Kidney Cells in Response to SEB.
Figure 15:
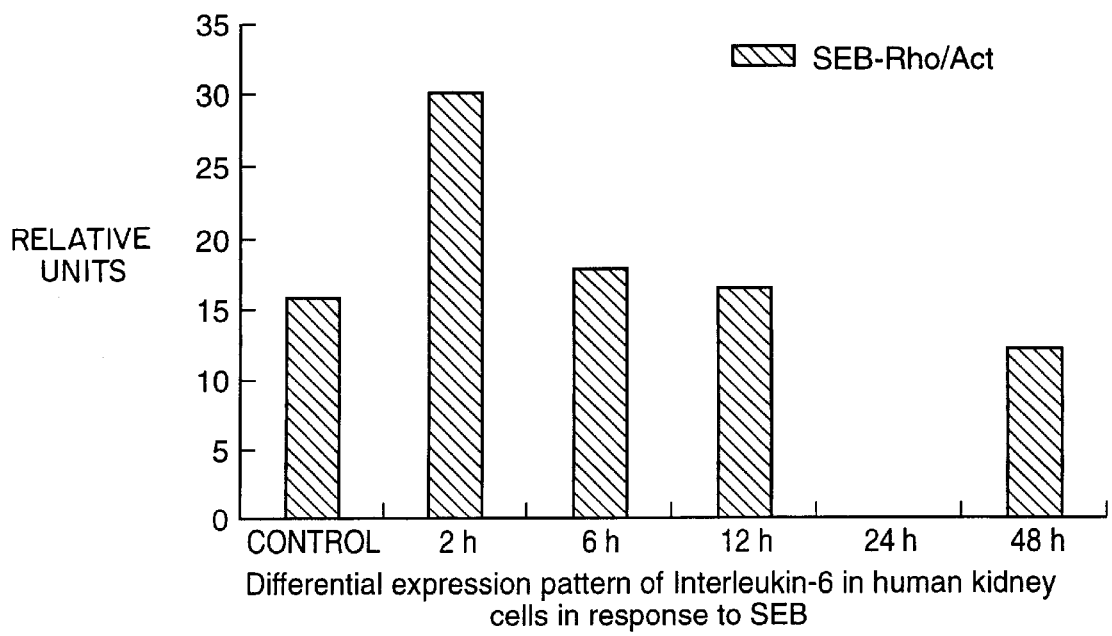
FIG. 15 is a graph showing a differential expression pattern of Interleukin-6 in Human Kidney Cells in response to SEB.
Figure 16:
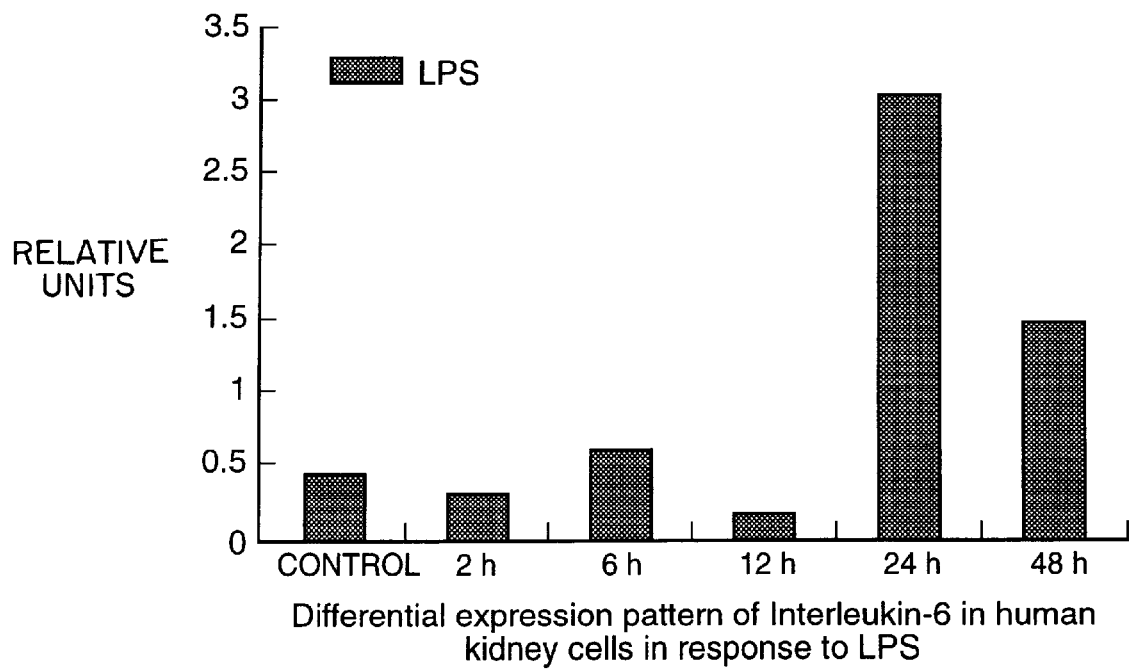
FIG. 16 is a graph showing differential expression pattern of Interleukin-6 in Human Kidney Cells in response to LPS.

The RhoE gene was identified by differential display (DD)—polymerase chain reaction (PCR) as one of the genes that was down regulated by SEB in renal proximal tubule epithelial cells (RPTEC). Two- to eight-fold reduction in expression, depending on the length of cell exposure to SEB, was confirmed by reverse transcription (RT)—PCR with specific primers (FIG. 14). Expression of RhoE gene was down regulated by SEB as early as 2 hrs (¼ th of control levels) and this was seen even after 72 hrs ($¼^{th}$ of control levels).

Comparison of Gene Expression Patterns Induced by LPS and SEB in Human Kidney Cells.

A) Genes encoding ferritin, Guanylate binding protein (GBP), and interleukin-6 (IL-6) were differentially expressed in RPTEC (renal proximal tube epithelial cell) stimulated with LPS. The peak expression of ferritin and GBP occurred at approximately 6 h of exposure, while the IL-6 did not show significant levels of expression until 24 h of the toxin stimulation. None of these genes were differentially expressed in cells stimulated with SEB, as compared to the control cells (FIGS. 15–18).

B) Genes encoding hypoxia-inducible factor-1 (HIF-1) and myosin heavy chain showed no significant differences in expression patterns in LPS-stimulated RPTEC. However, both of these genes were up regulated in SEB-stimulated cells, with peak expression of HIF-1 and myosin occurring at approximately 2 h (greater than two-fold increase over control) and 24 h (greater than 20-fold difference increase over control), respectively (FIGS. 19–20).

Figure 17A:
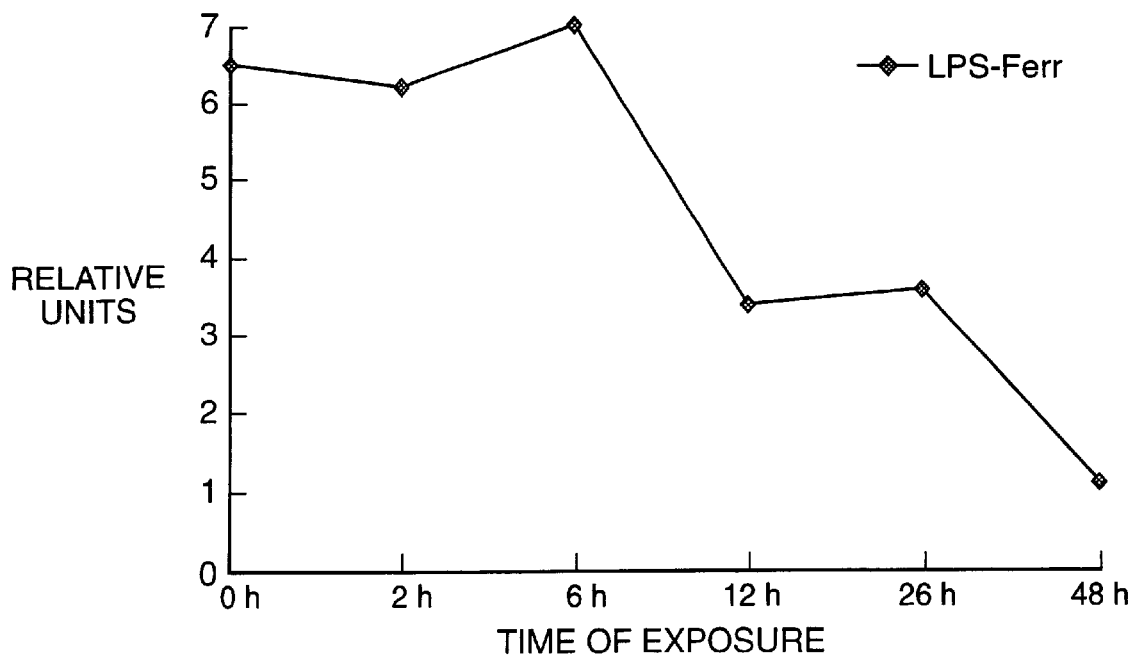
FIG. 17a is a graph showing the expression pattern of Ferretin Heavy chain in kidney cells in response to LPS.
Figure 17B:
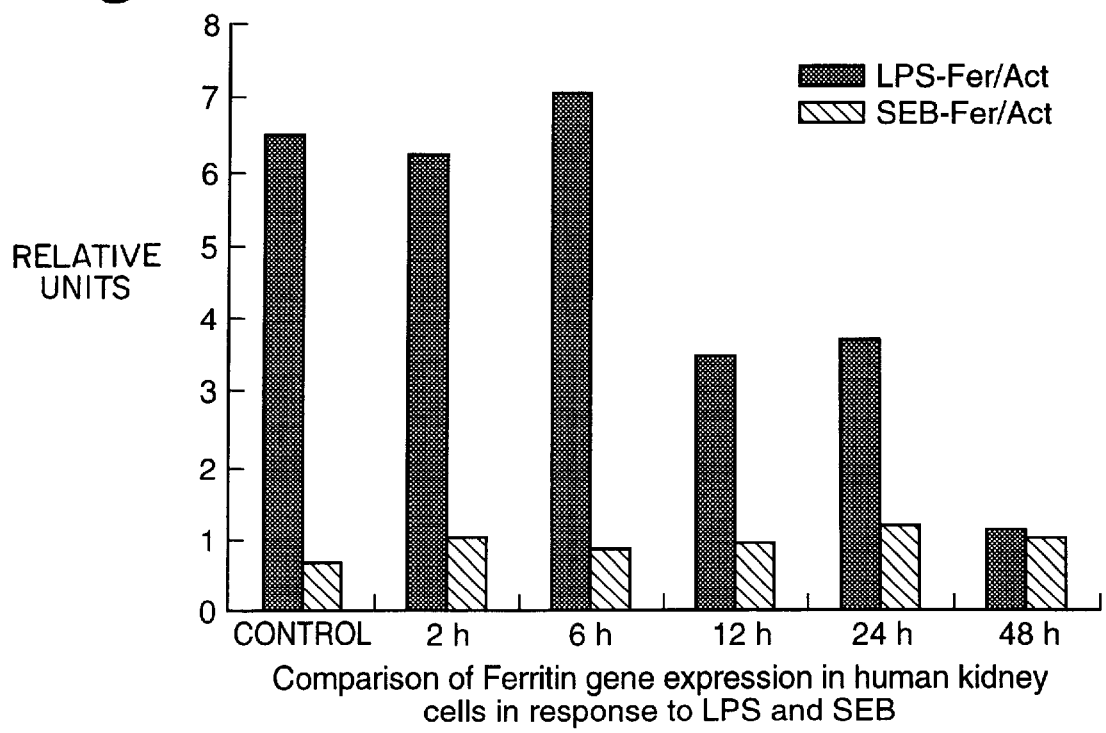
FIG. 17b is a graph showing comparison of Ferritin Gene Expression in human kidney cells in response to LPS and SEB.

In FIG. 17b, for each pair of results shown comparing Ferritin gene expression in response to SEB and LPS, the left band is LPS-FER/Act and the right band is SEB-Fer/Act.

Figure 18:
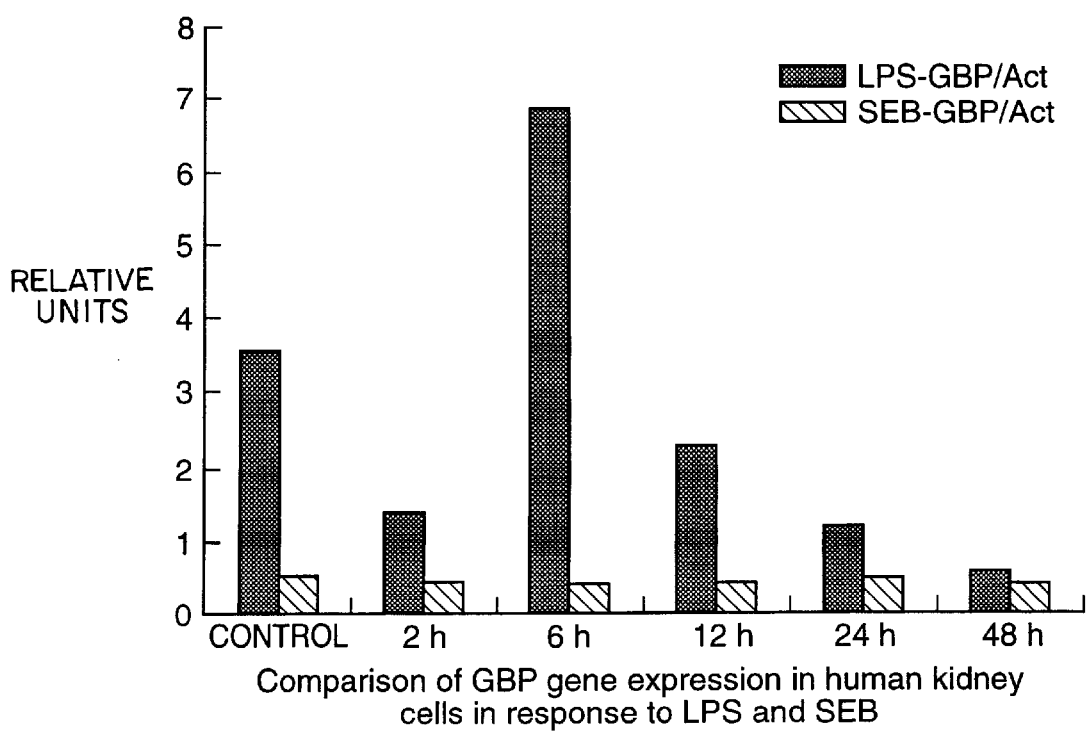
FIG. 18 is a graph showing comparison of GBP gene expression in human kidney cells in response to LPS and SEB.

In FIG. 18, for each pair of results shown comparing GBP gene expression in response to LPS and SEB, the left band is LPS-GBP/ACT and the right band is SEB-GBP/Act.

Figure 19:
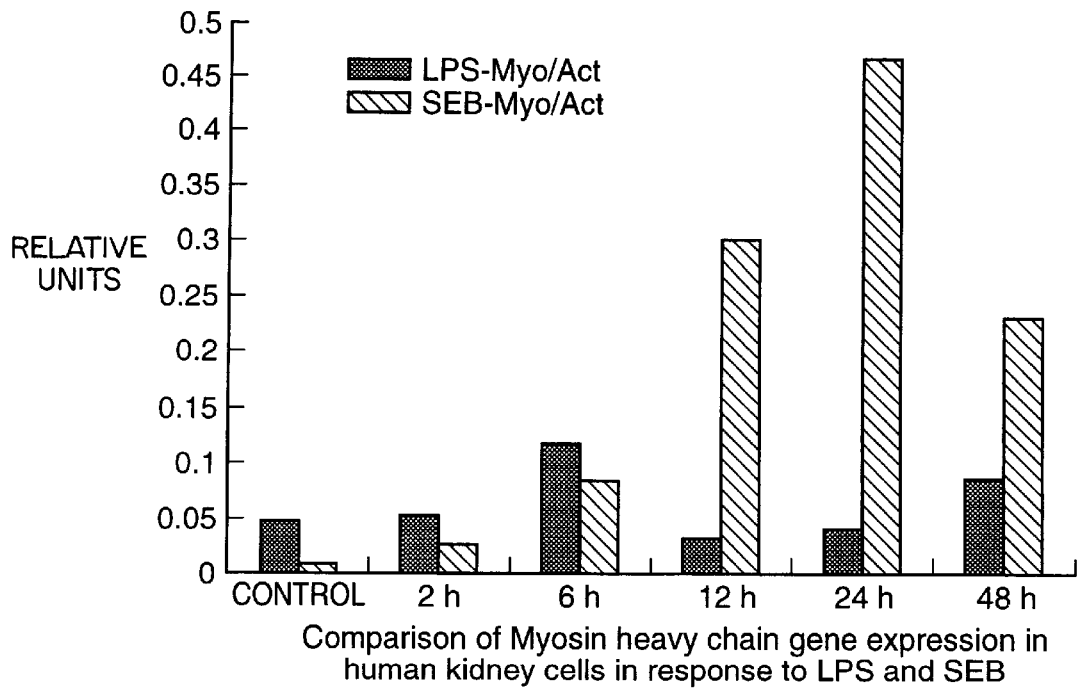
FIG. 19 is a graph showing comparison of Myosin Heavy chain Gene Expression in human kidney cells in response to LPS and SEB.
Figure 20:
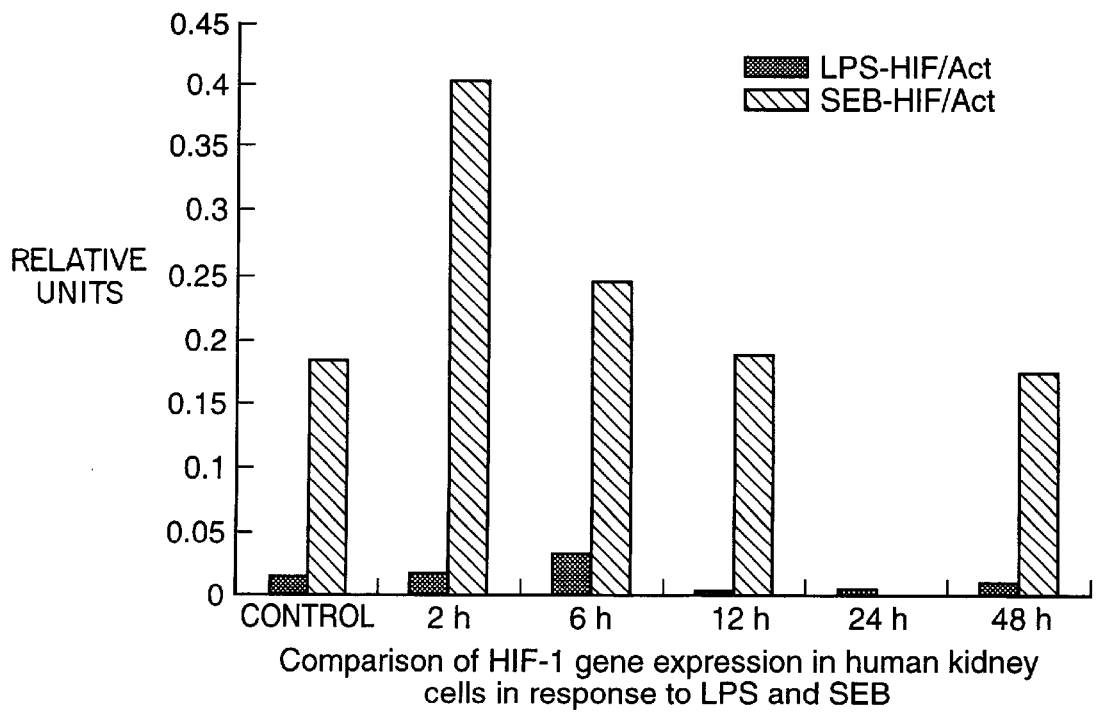
FIG. 20 is a graph showing a comparison of HIF-1 gene expression in human kidney cells in response to LPS and SEB.
Figure 21:
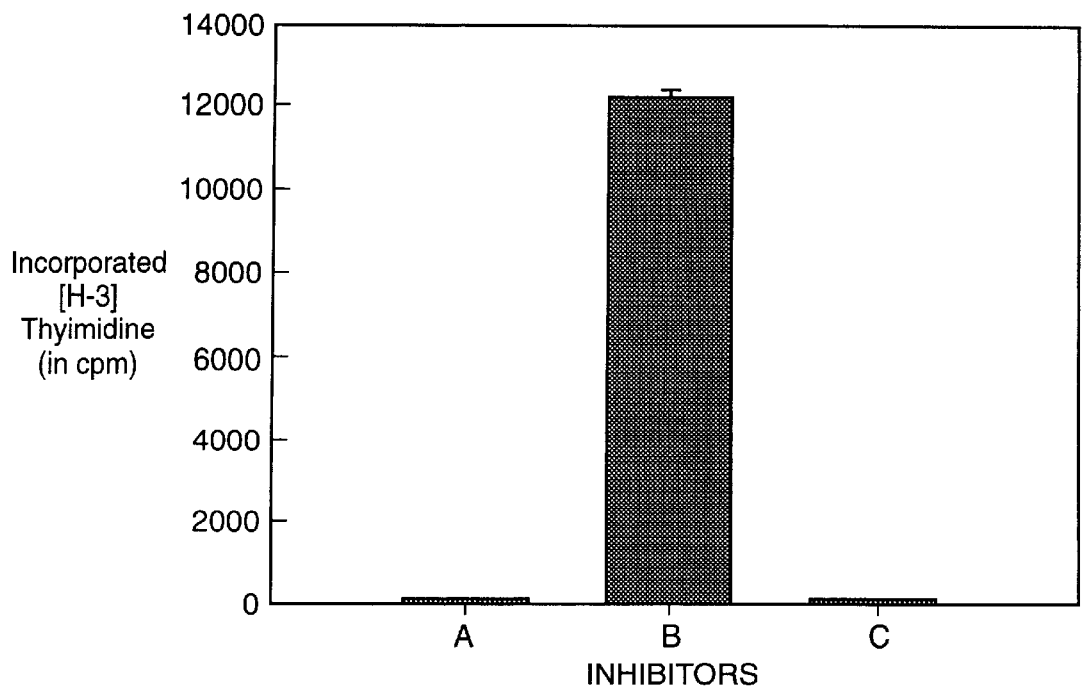
FIG. 21 is a graph showing the effect of P-38 in SEB induced cell proliferation.
Figure 22:
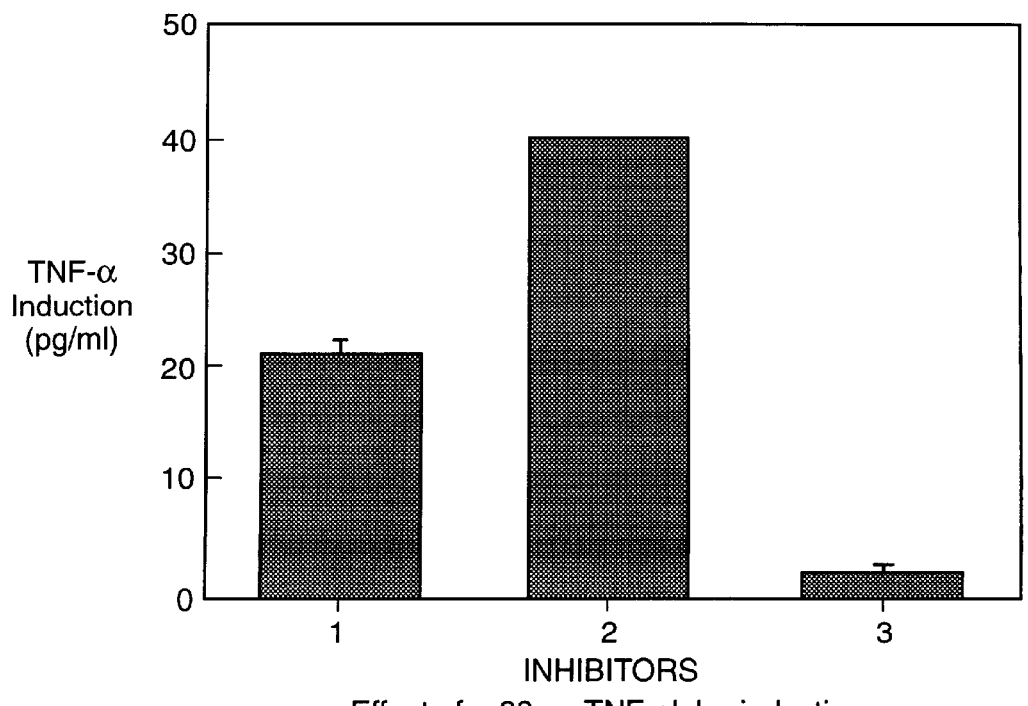
FIG. 22 is a graph showing the effect of P-38 on TNF-alpha induction.
Figure 23:
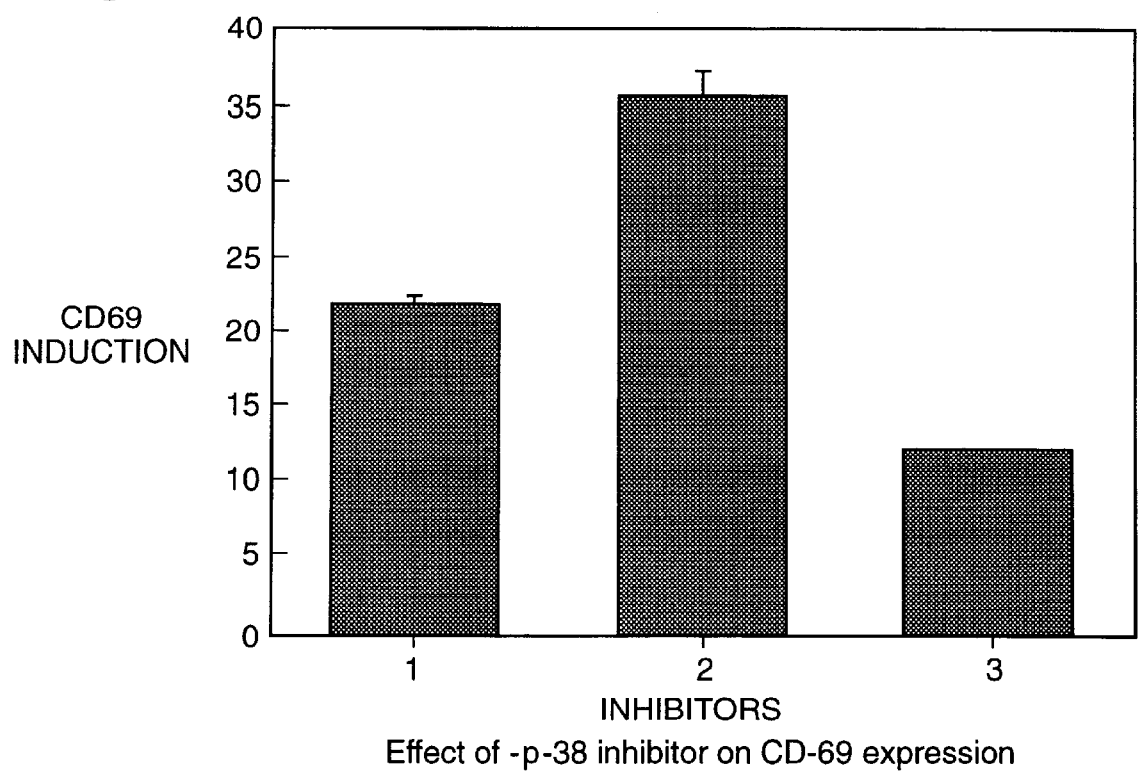
FIG. 23 is a graph showing the effect of P-38 inhibitor on CD-69 expression.
Figure 24:
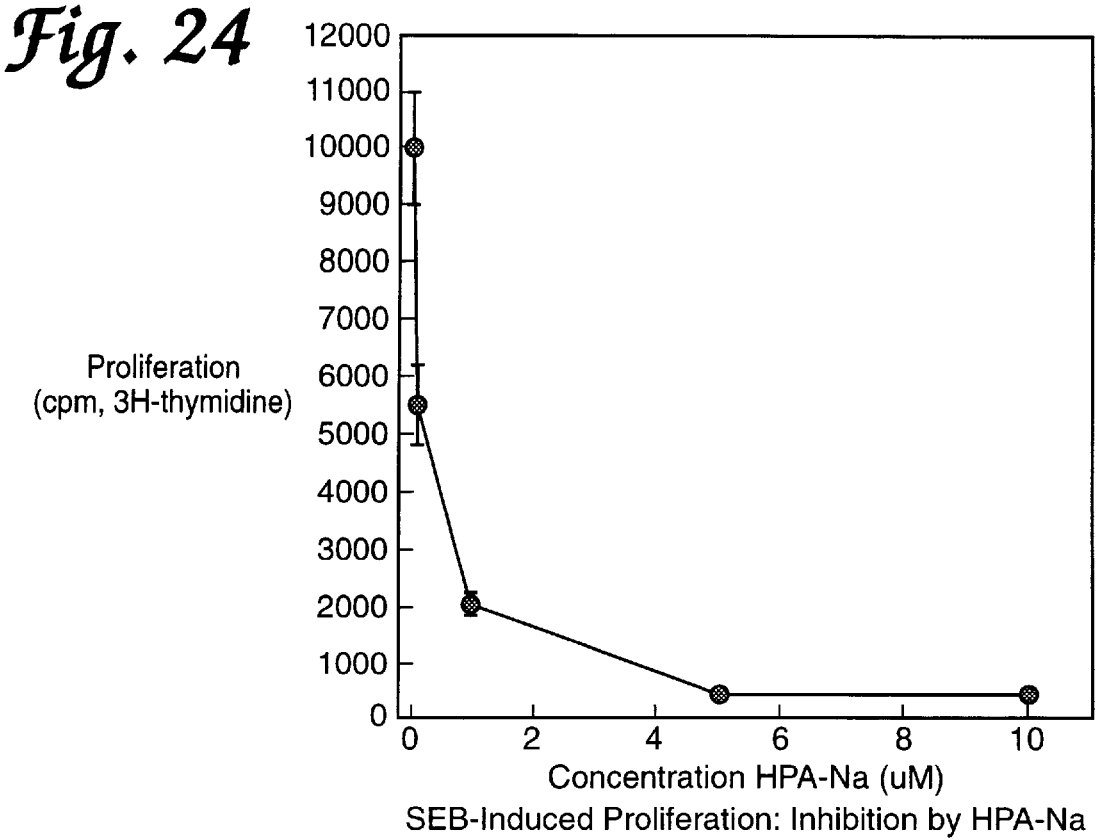
FIG. 24 is a graph showing SEB-induced proliferation: inhibition by HPA-Na.
Figure 25:
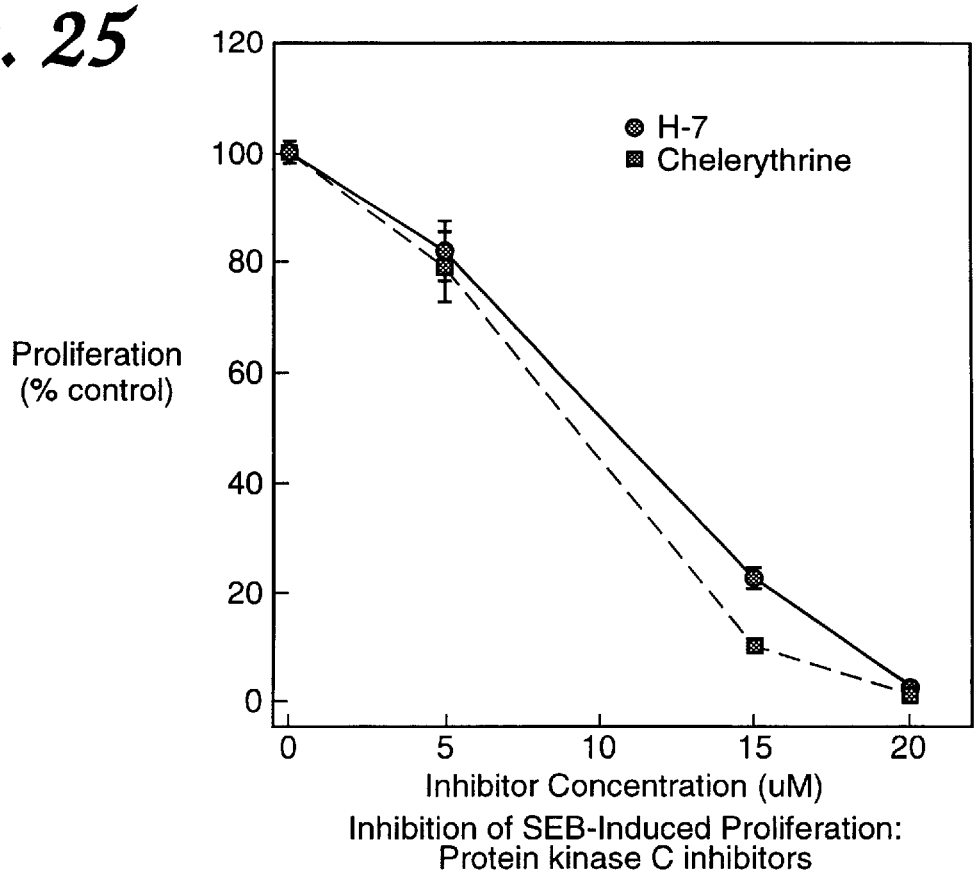
FIG. 25 is a graph showing SEB-induced proliferation: protein kinase C inhibitors.
Figure 26:
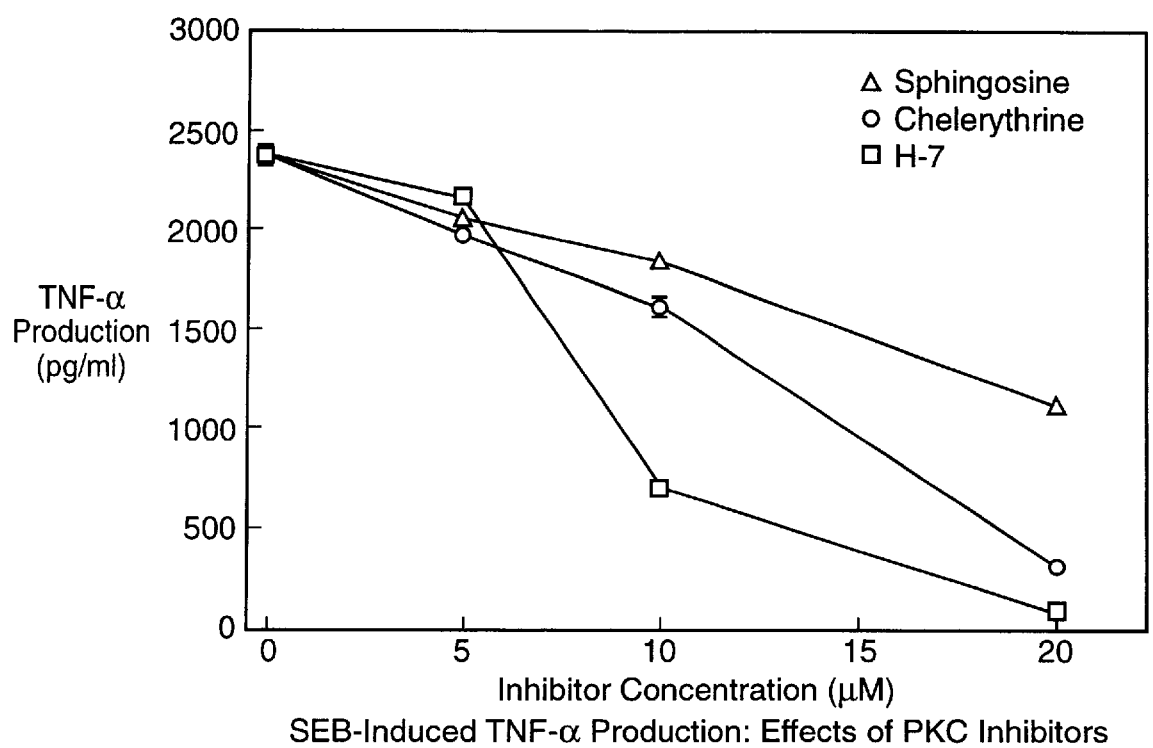
FIG. 26 is graph showing SEB-induced TNF-α production: effects of PKC inhibitors.
Figure 27:
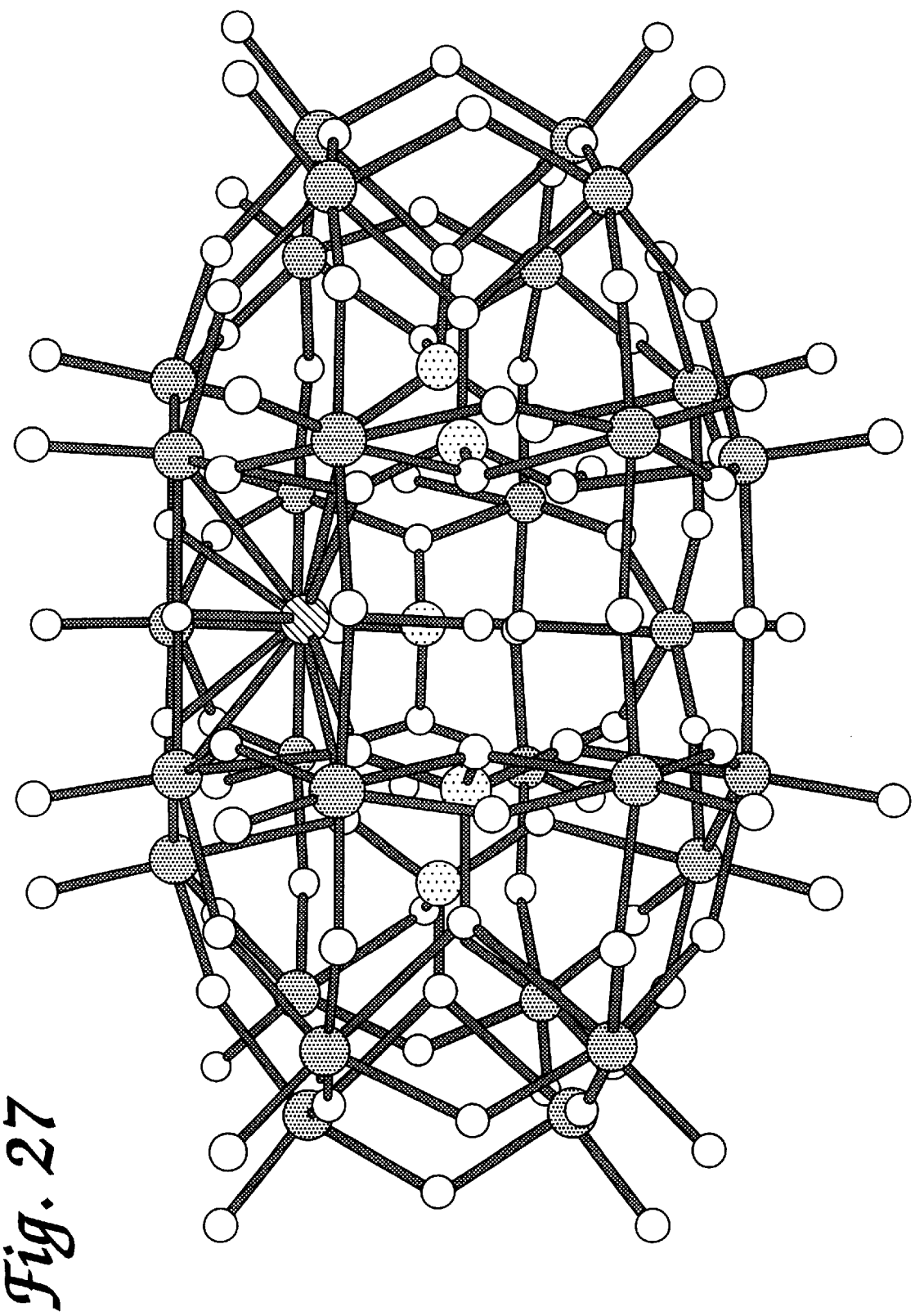
FIG. 27 is a model of HPA-Na molecule.

In FIG. 19, for each pair of results showing the comparison of myosin heavy chain gene expression in human kidney cells in response to LPS and SEB, the left band is LPS-Myo/Act and the right band is SEB-Myo/Act.

In FIG. 20, for each pair of results showing the comparison of HIF-1 gene expression in human kidney cells in response to LPS and SEB, the left band is LPS-HIF/Act and the right band is SEB-HIF/Act.

Summary of Gene Changes in Human Kidney Cells in Response to SEB:

Table 4 summarizes all the 32 genes that were altered in kidney cells in response to SEB exposure. There were 14 genes that were up regulated and 18 genes that were down regulated.

Effect of Drugs to Block SEB Induced Responses:

We have tested three different drugs and have found them to be effective blockers of SEB induced responses. P-38 inhibitor is a inhibitor of a kinase that is crucial for signal transduction of SEB in human lymphocytes. HPA-Na is a heteropolyanion that is a free radical scavenger that is also very effective in blocking the SEB effects.

Effect of P-38 Inhibitor on SEB Induced Cellular Events:

The drug known as P-38 was obtained from Smith Klien Beecham, N.J. Human TNF—α can either be as a membrane associated (26 kDa) or secreted (17 kDa) form (Kriegler, et al., cell, 53, 45–53, 1988). TNF-α induced by SEB is in the secreted form. TNF-alpha induces hemorrhagic necrosis and regression of tumors in animals, is cytotoxic to transformed cells, and promotes immunity, inflammation, insulin resistance, hypertension, shock and some cases chronic diseases (Tracey, et al., Annu. Rev. Cell Biol., 9, 317–343, 1993; Sidhu, et al., Pharmacol. Ther., 57, 79–128, 1993). Ability of P-38 inhibitor to block: the induction of TNF-alpha makes this a solid therapeutic target.

Cells of the immune system utilize surface molecules for selective trafficking and focused cellular responses to a variety of inflammatory stimuli (Hogg, et al., Curr. Opin. Immunol., 5, 383–589, 1993; Mackay, et al., Immunol. Today, 1, 99–104, 1993). CD69 is a surface molecule that is rapidly expressed in response to various interl,ukins such as IL-2, IL-13 and is closely linked to the activation to protein kinase C in human T lymphocytes (Bjorndahl, et al., J. Immunol., 1, 4094–4098, 1988; Cebrian, et al., Eur. J. Immunol., 19, 809–816, 1989; Hamann, et al., J. Immunol., 150, 4920–4928, 1993; Testi, et al., J. Immunol., 150, 4920–4924, 1989). Flow cytometry is used for assessing surface molecule expression on selected cell populations. Ability of P-38 kinase inhibitor SB-203580 to reduce the production of CD69 induced by SEB increases the importance of P-38 inhibitor as a therapeutic target.

Effect of P-38 Inhibitor on SEB Induced Responses:

Effect of p-38 Inhibitor on Cell Proliferation.

P-38 inhibitor was administered at a concentration of 10 uM. P-38 inhibitor was able to block the growth of T-cells as shown in FIG. 21. Induction of cell proliferation by SEB as shown in FIG. 21 (12,000 cpm) was clearly inhibited with the treatment of SEB induced cells with 10 uM of p-38 inhibitor SB-203580 (FIG. 21).

Effect of P-38 Inhibitor on the Induction of TNF-alpha

Upon the treatment of SEB with P-38, the TNF-$\alpha$ gene expression in human lymphoid cells almost doubled compared to untreated samples. When treated with 10 $\mu$g of P-38 inhibitor, the previously observed induction of the TNF-$\alpha$ gene by SEB was brought down back to control levels (FIG. 22).

Effect of p-38 Inhibitor on the Induction of CD-69

When treated with 100 ng/ml SEB, we observed a clear stimulation of CD69 production in human lymphoid cells (15–20 pg/ml over control levels). This induction with SEB was clearly blocked upon the treatment with 10 uM of P-38 inhibitor (FIG. 23).

Effect of HPA-Na and PKC Inhibitors on SEB Induced Responses:

SEB is known to induce rapid proliferation of the T cells, we tested different concentrations of the drugs on this assay and showed a definite decrease in proliferation. (FIGS. 24, 25) We also showed that the PKC inhibitor was able to block effectively TNF-alpha production upon exposure of human peripheral blood lymphoid cells (isolated monocytes/lymphocytes:1/4) to SEB as well. H7 was the inhibitor that was most effective among the other PKC inhibitors (FIG. 26).

Effect of HPA on Proliferation Assay Induced by SEB:

The drug HPA-Na was given in the amount shown in FIG. 24 and was able to block the SEB induced T cell proliferation which was tested by thymidine incorporation. The drug HPA-Na was chosen in the laboratory out of a panel of several of these group of heteropolyanions. As shown in FIG. 24, HPA-Na was effective at very low concentrations to Iblock the proliferation of lymphoid cells induced by SEB.

The drug HPA-Na (a heteropolyanion which is a metal ion derivative of polyoxotungstate) was synthesized in the laboratory using methods outlined in Heteropoly and Isopoly Oxometalateds, Michael Thor Pope, Springer Verlag, Berlin, Crerrnany 1983. This drug is water soluble and stable at room temperature. Its structure is shown in FIG. 27.

Effect of Inhibitors of Protein Kinase C:

As shown in FIG. 25, these inhibitors (H-7 and Chelerythrine) effectively blocked SEB-induced proliferation. As shown in FIG. 26, these inhibitors also blocked production of TNF-$\alpha$ and also blocked production of eicosanoids and neuropeptides.

Treatment of Toxin Induced Illness with Antisense:

A new technique for treating patients is to prevent expression of specific genes by administering antisense to the MRNA for that particular gene. For the situation described in this document, persons exposed to toxic agents, in addition to classical drugs that target specific metabolic pathways, could be treated with antisense to MRNA coding for specific genes that we have determined to be critical for toxicity induced by the specific toxic agent. An example is that staphylococcal enterotoxin B illness is characterized by rapid drop in blood pressure, likely due to loss of regulation of vascular tone especially in organs. We have identified several genes, with altered expression in response to SEB that are involved in various aspects of regulation of vascular tone (Table—). Another example of a more severe progression of SEB-induced illness is respiratory distress (leading to death); we have also found SEB-induc ed alterations in expression of genes that have been related to respiratory distress (Table—).

First one would determine, based on gene array analysis or conventional structural-based probes, that the patient had been exposed to a toxic agent. If gene array analysis had been performed, detection of expressed genes known to be critical for the progression of the intoxication would be apparent.

Dose of antisense: Typically patients have been treated and tolerate a dose of 0.5–3 mg/kg/day delivered by continuous intravenous infusion. In most cases for the toxic agents, there is a critical time period of the illness that lasts for 2–4 days. Treatment with antisense therapy for this length of time would not present a problem. One study treated ovarian cancer patients for 21 days on/7 days off (Yuen, et al., Yuen AR, et al., Phase I study of an antisense oligonucleotide to protein kinase C-alpha (ISIS 3521/CGP 64128A) in patients with cancer, Clin Cancer Res 1999 Nov., 5(11):3357–63 (1999). Other methods of administration are also under study including intraperitoneal, intramuscular and oral administration.

Antisense (complementary base pairs to the desired sequence) is typically constructed beginning with the 3 base “start code” for a specific MRNA and proceeding with the nucleotide sequence of the MRNA for the gene in question. Using Blast and other Gene search engines, one continues down the sequence of the desired gene until one determines that the sequence targets only the mRNA for the desired gene. An example in our laboratory is that for liver-fatty acid binding protein (L-FABP), a 19 base oligonucleotide sequence wvas specific for L-FABP. Hammameih, FASEB J. in press.

In general, this approach is successful because the antisense fragment binds to the complementary region of the selected gene. At that point, several theories exist such as that RNases are activated due to the complementary oligonucleotide bound to the mRNA or that blocking the “start code”, along with binding of the complementary oligonucleotide to the selected gene, prevents mRNA synthesis. Never the less, extensive studies indicate that directed antisense blocks synthesis of the gene in question. Shi Q, et al., Constitutive and inducible interleukin 8 expression by hypoxia and acidosis renders human pancreatic cancer cells more tumorigenic and metastatic. Clin Cancer Res 5(11):3711–21 (1999); Cho-Chung YS, Antisense DNA-targeting protein kinase A-RIA subunit: a novel approach to cancei treatment, Front Biosci 4:D898–907 (1999); Tian XX et al, Altered expression of the suppressors PML and p53 in glioblastoma cells with the antisense-EGF-receptor. Br J Cancer 81(6):994–1001 (1999).

Additionally, some of the genes (and their corresponding proteins) found to be altered in response to toxic agents have already been studied for other reasons and specific inhibitors exist to treat the toxic agent-induced illness. Respiratory distress induced by SEB (see Table 1) is an example. Although no one knew previously that these genes and their corresponding proteins were altered in response to SEB, these mediators were well known to be involved in asthma-induced respiratory distress. As such, specific inhibitors have been and are being designed to target these products.

Intravenous administration of antisense therapy is likely to be the most successful route since most of the action of toxic agents might be expected to be associated with lymphoid and endothelial cells. In addition, IV could be distributed to the kidney, liver and spleen.

Effect of Anthrax on Expression of Different Genes in Human Lymphoid Cells:

Cells were exposed to anthrax spores for different time periods and RNA isolated from the cells. Primers were designed for each gene and RT-PCR performed on RNA samples from different time periods of Anthrax exposure. Gene expression of Ferritin heavy chain and GBP did not alter in response to Anthrax (FIGS. 28, 30). However expression of HIF-1 was up regulated within two hours and reached its peak by 8 hrs and was constant till 24 hrs (FIG. 29). Expression of IL6 was increased moderately doubling by 24 hrs (FIG. 31) in anthrax treated cells.

Genes identified from differential display in anthrax treated cells were also tested for the level of expression by RT-PCR. FIG. 32 shows the expression of ILT6 (immunoglobulin-like transcript) to be significantly up regulated by 6 hrs and it reaches its peak at 12 hrs of anthrax exposure. The expression of cathepsin-L (a lysosomal enzyme) was also shown to be up regulated in FIG. 33a. There was a dramatic decrease in expression of HCI (Human collagenase inhibitor) and EIF3 (eukaryotic translation initiation factor) upon Anthrax exposure (FIG. 33b).

Comparison of Gene Expression Pattern in SEB and Anthrax Treated Cells:

The expression of GBP was compared in SEB and anthrax treated cells. There was a significant difference in response in these two sets. SEB showed an up regulation of the gene however there was no change in expression of the gene in anthrax treated cells (FIG. 34). This suggests that there is a pattern of changes in gene expression, which will be specific for each agent.

Figure 35:
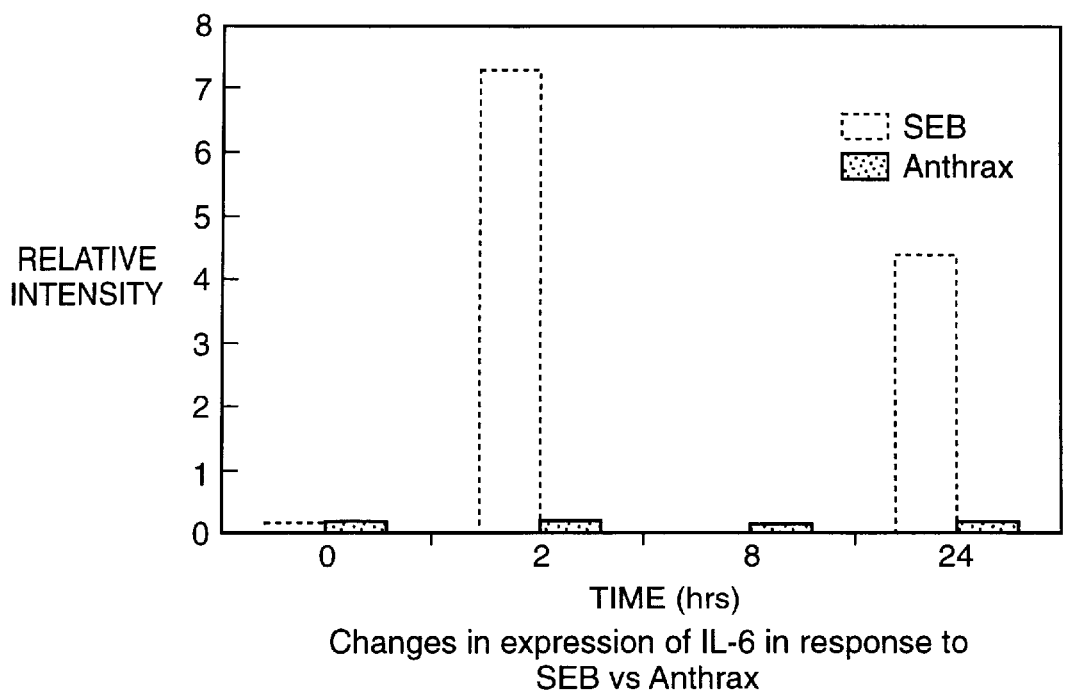
FIG. 35 is a graph of the change in expression of IL-6 MRNA in response to SEB vs Anthrax.

Expression of IL6 was compared in cells exposed to these two BW agents. IL6 showed a 50-fold increase by two hours of SEB exposure and it remained high even after 24 hrs. There was no change of IL6 expression in two hours of Anthrax exposure however there was only a two fold increase by 24 hrs (FIG. 35). This suggests a distinct pattern of gene expression induced by each agent in a host cell.

Figure 36:
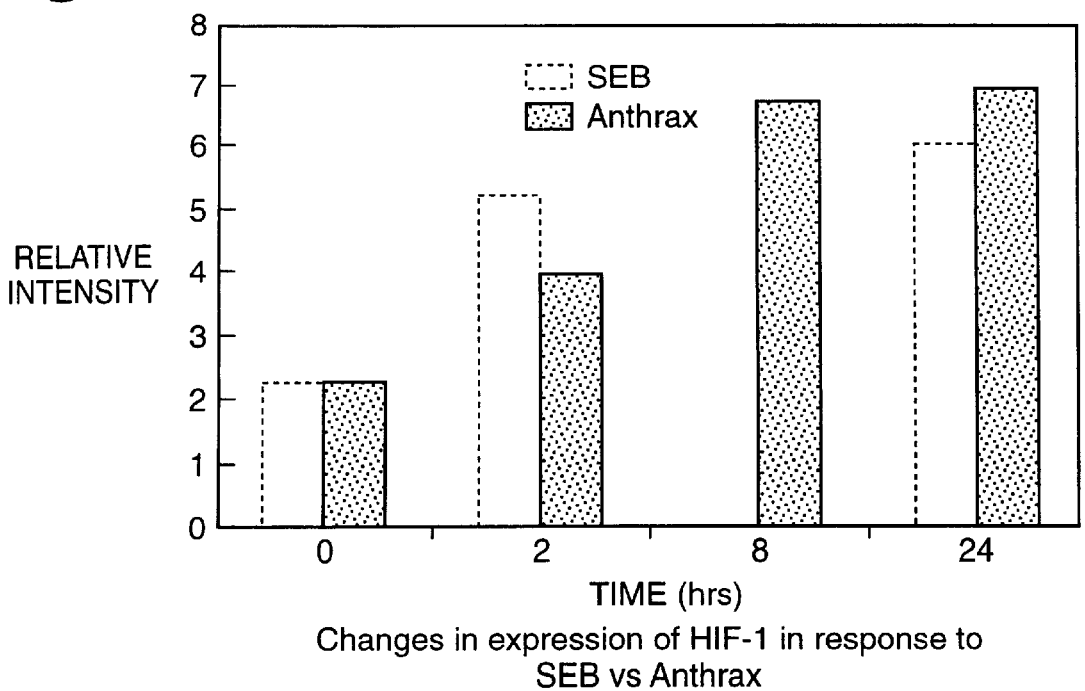
FIG. 36 is a graph of the changes in expression of HIF-1 in response to SEB vs Anthrax.

Expression of HIF-1 was up regulated in both the groups with SE B and Anthrax treated cells (FIG. 36). It is not surprising that certain genes are elevated in response to several, but not necessarily all the various toxins. We expect that these genes, while less specific for a particular agent, may still be useful to establish a pattern of alterations in gene expression by the various toxic agents.

In FIGS. 34–36, for each pair of results shown, the left band is SEB and the right band is Anthrax.

Differential Display Gel Profiles of each BW Agent:

RNA was isolated from lymphoid cells after treatment with each agent. RNA was processed using differential display kits (obtained from Beckman-Coulter, CA) using 33P to label the PCR products and was resolved on a long-read gel. The gels were dried and exposed to X-ray films.

Figure 37:
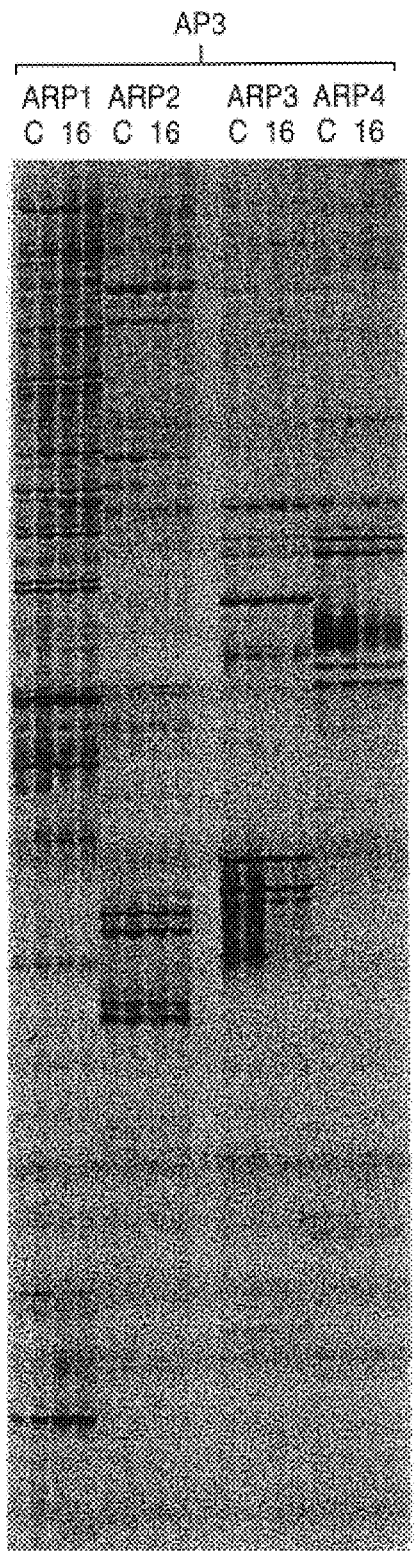
FIG. 37 is a digital differential display gel profile showing gene profiles of SEB exposed samples as compared to gene profiles of a control.

Cells were treated with SEB for 16 hrs and different AP (anchored primers) and ARPs (arbitary primers) primers were used for the DD-PCR reaction (FIG. 37). Each reaction was performed in duplicate and the samples were resolved on a 4.6% acrylamide gel. Bands that were altered were cut, cloned and analyzed for their sequence. On the digital display, the 'C' represents a control and the ARP# represents a sample exposed to SEB.

Cells were treated with anthrax spores for 12 hrs and RNA isolated and compared to the control at 12 hrs. The comparison of SEB and anthrax is shown in FIG. 38. Bands of interest were cut out and identified for gene sequences.

Monocytes were exposed to Yersinia pestis for 30 mins. and were inactivated in gentamycin for two hours prior to RNA isolation. Combination of different APs and ARPs were used on these RNA samples in duplicate and resolved on a long gel. Bands that showed changes were cut out for further analysis (FIG. 39).

Figure 40A:
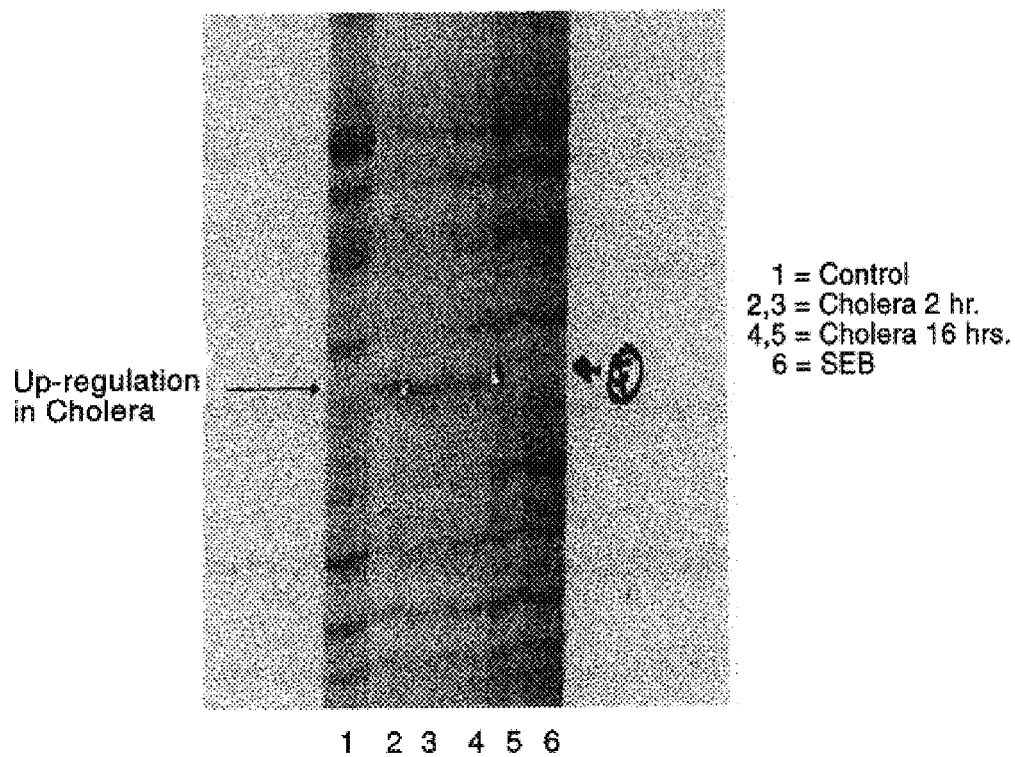
FIG. 40a is a digital differential display gel profile showing gene profiles of cholera toxin exposed samples as compared to gene profiles of a control.
Figure 40B:
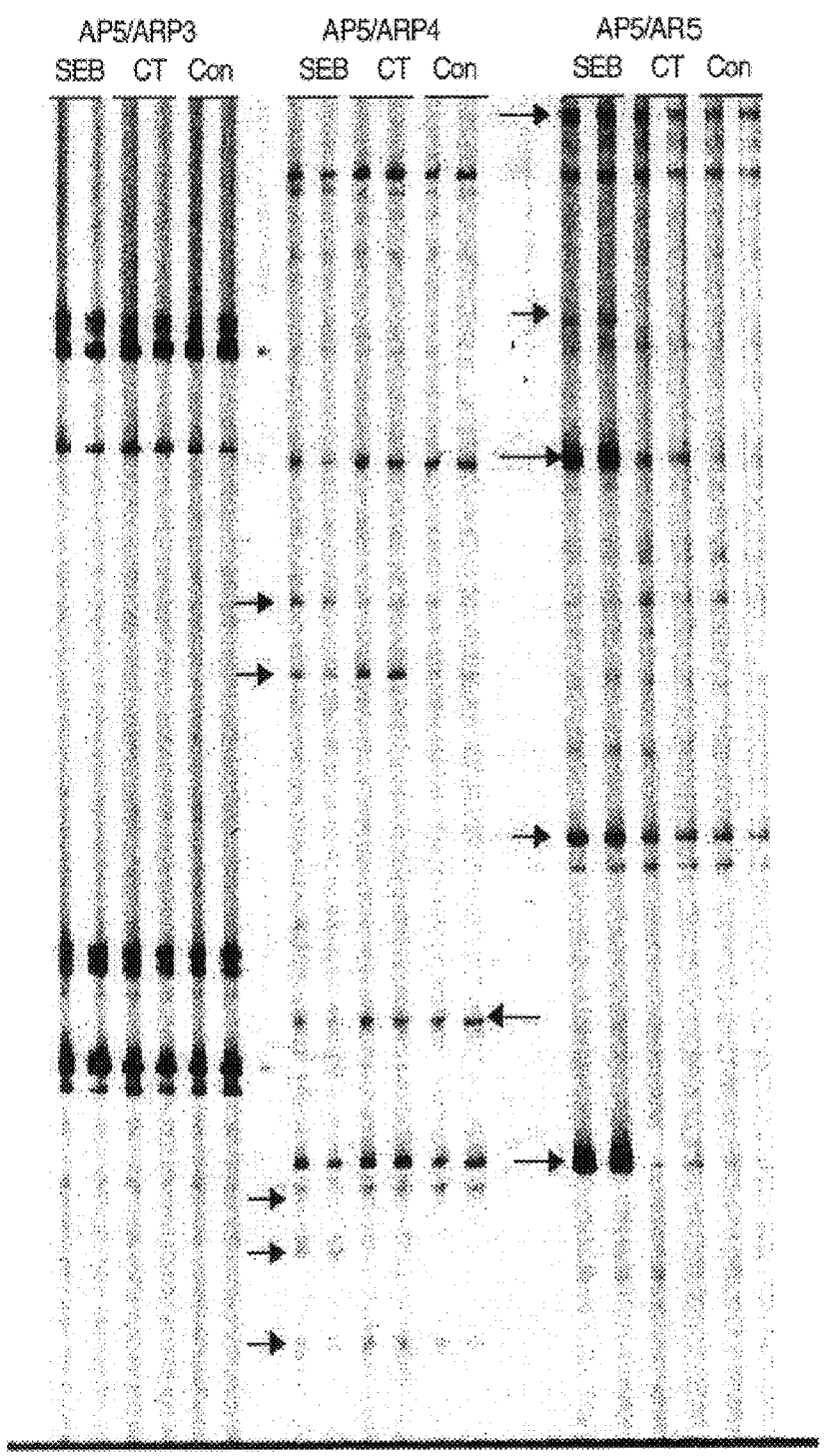
FIG. 40b is a digital differential display gel profile showing comparison of changes in gene expression in response to SEB and Cholera Toxin.

Lymphoid cells were exposed to Cholera toxin for 12 hrs prior to RNA isolation. DD-PCR reaction was performed and resolved on a long gel. Bands of interest were isolated and purified for sequencing (FIG. 40).

A prototype example is described using 2 shock-inducing; toxins, staphylococcal enterotoxin B (SEB) and endotoxin, of which lipopolysaccharide (LPS) is the smallest active unit.

a) Gene profile for diagnostics: We determined the changes in gene expression in response to two shock-inducing toxins, staphylococcal enterotoxin B (SEB) and lipopolysaccharide (LPS), the smallest active unit of endotoxin. For these two agents which result in lethal shock using different mechanisms, we found several alterations in lymphoid cell gene expression which are common to both. However, we have also found genes that are specifically altered by each agent. We found that patterns of gene expression in lymphoid cells could be categorized to indicate likely course/outcome (such as shock, neurological toxicity, etc) very early after exposure to a toxic agent.

b) Gene identification for treatment: Lethal shock has proven to be elusive in successful treatment because so many cascades of cellular mediators are activated; the techniques we have used, differential display (DD)-PCR have identified genes never before thought to be involved in shock. Several of these genes contribute to regulation of vascular tone (hypotension is one of the major problems with lethal shock). We realize that manipulation of the expression of the corresponding proteins offers new targets for treatment of shock.

c) Novel previously unknown genes: We have found many genes responding to SEB which are not yet in the databases although they show up as gene bands on polyacrylamide gel. These novel genes have been sequenced and present additional possibilities for treatment.

d) We have tested this approach using peripheral blood lymphoid cells isolated from monkeys challenged with SEB. We selected genes to verify based on the experiments using DD-PCR with SEB exposure. Indeed, as early as 30 min. post-SEB exposure, we observed that the in vivo response reflected the pattern of altered gene expression that we had seen in vitro.

At the present time we have now found about 43 gene with altered expression, which have been observed upon SEB exposure to peripheral blood human lyniphoid cells. Of these genes, the identity of 9 genes has been determined by comparing their sequences to known sequences in GEN- BANK databases. Those genes have never previously been associated with SEB-induced lethal shock.

We have also identified 85 genes appearing as bands on gel in anthrax exposure to peripheral blood human lymphoid cells and 28 bands on gel in Plague exposure to peripheral blood human lymphoid cells and about 30 bands on gel in Cholera exposure to peripheral blood human lymphoid cells, each band indicating a specific gene. See FIGS. 37–40b.

These peripheral blood human lymphoid cells can be obtained readily from patients and provide a reservoir of information due to their responses to toxins, infectious agents, etc.

We have catalogued patterns of responses for several toxins; the objective was to relate genes expressed in response to a biological warfare insult, to a map of responses predictive of physiological responses. Examples of maps of responses are shown in FIGS. 37–40b. Each gene on the map appearing as a band. The band pattern that shows SEB exposure is different than the band pattern for anthrax, cholera, etc. Since each band contains a particular gene, the gene pattern for SEB for example, can be placed on a DNA chip for use in field diagnosis of toxin exposure.

One need not know the identity of the toxic agent to determine the likely progression of symptoms, based on markers/mediators induced. The advantages in screening for specific mRNA for diagnostic markers induced by BW agents is that it will provide a target for early detection of surrogate markers of impending illness. Having identified what genes are effected by the toxins, we are able to design strategies for treatment approaches to block their function and thus prevent the lethal shock.

Advantages Of The Invention Over Current Processes:

Structural based probes may not identify biologically altered toxic agents and most certainly will not detect trace levels of potentiating agents which have the ability to dramatically enhance toxicity. Use of the present system in which host response to exposure is examined, not only takes into account bioengineered agents or contaminants, but also assists in designing appropriate treatment based on factors such as degree of exposure and the individual response to the toxic agent.

Problems Which The Invention Is Designed To Solve:

Identification of toxic agents which have the potential to be used in terrorist attacks or accidental exposures, have previously been based on structural characteristics of the known toxic agents. Because of the threat of biologically altered toxic agents or undetectable levels of trace potentiating contaminants, we have proceeded to develop alternate approaches which rely on an individual host's response and is independent of the need to determine which toxic agent is present. Instead, the type of impending illness (shock, neurological toxicity, etc) can be determined by analyzing gene expression patterns of the peripheral blood lymphoid cells from exposed individuals. In vivo, we have seen gene expression patterns that are indicative of shock as early as 30 min post-SEB exposure. For in vitro studies, we chose 2 hr post exposure as the first time period; we also examined 16 hr, 24 h and later time periods as well.

Predicting exposure of a person to these agents before the symptoms appear will be of great advantage for timely treatment which can decrease morbidity and mortality from exposure to toxic agents. As stated above, these genes can be places on a blot or a small DNA chip that can be used for screening blood cell samples for rapid detection.

Other Uses For The Invention:

In the studies carried out so far, SEB and LPS induced gene alterations were compared since both agents can lead to lethal shock. Exposures to SEB can be detected based on host response and tailored treatment designed Septic shock, induced by LPS from gram negative bacteria, is a usual emergency room occurrence daily; perhaps >20% of all emergency room cases are related to septic shock. Over at least the past 30 years, the finest pharmaceutical companies in the world have vigorously pursued studies to identify intervention tactics for septic shock; successes have occurred mainly for early stages of shock. We have now identified genes, never before associated with lethal shock, that directly influence vascular tone (possibly the most critical element of lethal shock). Targeting these genes provide new approaches to combat this deadly illness.

Novel Aspects Of The Invention:

We have identified a panel of host genes altered in response to BW agents that can be used as diagnostic markers. This has not been previously described. The advantages in screening for specific mRNA markers induced by toxic agents is that it provides a target for early detection of surrogate markers of impending illness. Having identified what genes are effected by the toxins, we are able to design strategies for treatment approaches to block their function and thus prevent the lethal shock.

Patterns of Mediator Production Reflect Exposure to a Specific Toxic Agent:

We had previously observed that various toxins produced a distinctive pattern in production of mediators of illness when using either cultures of human lymphoid cells or when using plasma and/or lymphoid cells from animal experiments. It is impractical to try to measure mediators produced because a) they appear, usually transiently, from minutes to hours or days and b) they are usually unstable. Therefore, we decided to create a library of responses to toxins using MRNA, which has none of the problems associated with the mediators, themselves.

Patterns of Gene Expression Reflect Exposure to a Specific Toxic Agent:

We found that each toxic agent alters gene expression in the host in a unique pattern. Lymphoid cells provide a readily accessible reservoir of information that can reveal direct or indirect responses to toxic agents. As prototype toxic agents in our initial studies, we assessed the biologic effects on lymphoid cells by certain toxins that induce lethal systemic shock in primates. Though different mechanisms staphylococcal enterotoxin B (SEB) induce production of a cascade mediators whose activities lead to shock. The release of endotoxin, of which lipopolysaccharide (LPS) is its smallest active unit, from the cell wall of gram-negative bacteria, and subsequent production of numerous host mediators, is the initiating event of septic shock (Pugin, J., C. C. Schurer-Maly, D. Leturcq, and et. al. 1993. Lipopolysaccharide activation of human endothelial and epithelial cells is mediated by lipopolysaccharide-binding protein and soluble CD14. Proc Natl Acad Sci USA. 90:2744–2748; Wright, S. D., R. A. Ramos, P. S. Tobias, and et. al. 1990. CD14, a receptor for complexes of lipopolysaccharide (LPS) and LPS binding protein. Science. 249:1431–1433. 1990). In contrast, SEB acts as a superantigen, stimulating T cell proliferation (Jett, M., R. Neill, C. Welch, T. Boyle, E. Bernton, D. Hoover, G. Lowell, R. E. Hunt, S. Chatterjee, and P. Gemski. 1994. Identification of staphylococcal enterotoxin B sequences important for induction of lymphocyte proliferation by using synthetic peptide fragments of the toxin. Infect Immun. 62(8):3408–15.1994; Neill, R. J., M. Jett, R. Crane, J. Wootres, C. Welch, D. Hoover, and P. Gemski. 1996. Mitogenic activities of amino acid substitution mutants of staphylococcal enterotoxin B in human and mouse lymphocyte cultures. Infect Immun. 64(8):3007–15. 1996), inducing a number of cytokine genes and other mediators in lymphocytes and monocytes (Yan, A., G. Yang, and M. Jett. 1997, Cholera toxin induces TNF-α production by human monocytes via cAMP independent pathways. FASEB J. 10:2746.). In our laboratory we have shown that SEB induces high levels of CD69 (Yan, 1997. Protein kinase C is involved in SEB induced TNF-α production. FASEB J. 10:1922) while LPS produces a minor change in this surface marker. In contrast, TNF-α production is rapidly elevated by LPS whereas SEB produces modest changes in its production (Yan). These changes which we have characterized are just a few of a battery of potential biomarkers indicative of patterns of impending illness. Production of a unique pattern of mediators of serious illness in response to toxic agents, is indicative of the type of illness or toxicity that will follow.

We have now proceeded to identify a spectrum of genes altered in response to toxic agents using the technique of differential display. Briefly, we have identified 43 altered genes in response to SEB; many of these genes differ from the genes activated by LPS. Furthermore, our studies with SEB have revealed completely new responses to the toxin which have never before been characterized and present new therapeutic approaches. We have further verified in monkeys challenged with SEB (compared with using each monkey as its own control in a saline sham), that the selected genes were altered as predicted in response to the toxin. These genes not only provide diagnostic capabilities for toxic agents, they indicate exposure dose, and also they also provide potential new targets for events that ultimately lead to SEB induced lethal shock.

Lymphoid Cells:

This approach centers on the fact that peripheral blood lymphoid cells can serve as a reservoir of historical information and can be readily obtained from an exposed individual. Furthermore, even though lymphocytes may not be the cells most affected by a biological, infectious or chemical agent, they tend to respond to BW agents by either direct or secondary stimulations. Indeed, certain tissues most affected by many toxic agents are inaccessible.

Our approach relies on determination of a battery of unique genes altered in response to each of the toxic agents. We have used staphylococcal enterotoxin B (SEB) as a prototype and have found 43 genes with significant alterations in expression upon exposure, in vitro, of human peripheral blood lymphocytes to the toxin (See FIG. 37). At this time, we have isolated, amplified, sequenced and identified from databases about 10 of these genes. One codes for the cytokine, IL-6, which has been extensively characterized as being increased in response to many shock-inducing toxins. The other identified genes have not been associated previously with staphylococcal illnesses or lethal shock and represent potentially new therapeutic targets as well as unique markers of SEB exposure for diagnostic purposes. We have verified these findings in lymphocytes of monkeys challenged with SEB; using PCR primers designed for the selected genes, we have found unique patterns in alteration of gene expression as early as 30 min post-aerosol challenge.

Global Library:

This invention provides for a library of gene responses to BW agents. These agents fall in to groups causing similar gene alterations for some agents, yet pin pointing unique responses with a battery of other genes. With SEB and LPS, IL-6, TNF-alpha and a few other mRNA changes, may not distinguish between the two shock-inducing toxins. In contrast 3 of 6 genes exhaustively examined to date show unique alteration in response to SEB and not to LPS. Selected genes act as markers, in a time-dependent manner, predicting the pattern of illnesses before the actual symptoms appear. Identification of specific genes that are differentially expressed in response to BW agents will reveal molecular pathogenesis that will enable us to design intervention to prevent or ameliorate impending severe illness. The molecular changes in the lymphoid cells with these prototype toxins can be eventually extended to other toxic agents and/or infectious agents that cause serious illness in humans.

We ha ve s hown changes in gene expression in lymphoid cells induced by SEB. We have shown changes in gene expression in kidney cells induced by SEB, and have confirmed the changes in monkey samples. We have compared the pattern in SEB with LPS induced changes in both the cell systems. We have also shown the effect of drugs to block the SEB induced effects in lymphoid cells.

Changes in Gene Expression Induced by SEB.

We decided to examine the changes in levels of gene expression induced by these toxins in order to move away fr om the inherent difficulties in quantitating cytokine changes a nd to try to identifh new therapeutic targets. Using SEB as a prototype, we studied changes in expression of mRNA using selected RT-PCR primers and subsequently performed the technique, differential display (DD). We have identified changes in expression patterns of 15 genes (9 up-and 6 down-regulated). To this date, the 9 shown in Table 1, have been isolated, cloned, sequenced and characterized.

TABLE 1

Changes in Gene Expression Identified in Lymphoid Cells Treated with SEB*

| GENE | PRIMERS | | CHANGES IN | |
| | Anchored | Arbitrary | EXPRESSION | FUNCTION |
| --- | --- | --- | --- | --- |
| #1 | AP3 | ARP3 | DOWN REGULATED | CTAP-III (gb MS4995), Involved in early stages of wound healing; has heparanase-like enzyme activity. |
| #2 | AP3 | ARP4 | DOWN REGULATED | Proteoglycan $V_1$ (EMB X15998), An adhesion molecule, which regulates vascular smooth muscle tone and is involved in lymphoid cell proliferation. |
| #3 | AP1 | ARP2 | UP REGULATED | A NOVEL GENE, No matching sequence have been found in either GENBANK and EMBL databases. |
| #4 | AP1 | ARP2 | UP REGULATED | IL-6 (gb M29150), A cytokine involved in inflammation, T-cell proliferation and release of cascades of other mediators |

TABLE 1-continued

Changes in Gene Expression Identified in Lymphoid Cells Treated with SEB*

| GENE | PRIMERS Anchored | Arbitrary | CHANGES IN EXPRESSION | FUNCTION |
|---|---|---|---|---|
| #5 | AP3 | ARP3 | UP REGULATED | Myosin 1 (emb AJ0013811), A contractile protein which has been characterized as contributing to cardiomyopathy; A regulator of motor activity. |
| #6 | AP3 | ARP3 | UP REGULATED | HIF-1 (gb AF050127), A protein which contributes to respiratory distress |
| #7 | AP3 | ARP4 | DOWN REGULATED | Currently no positive match with gene database |
| #8 | AP3 | ARP2 | UP REGULATED | Guanylate binding protein-2 (gb M5542), A protein which regulates cyclase activation |
| #9 | AP1 | ARP2 | UP REGULATED | Currently no positive match with gene database |
| #10 | AP3 | ARP2 | UP REGULATED | Currently no positive match with gene database |
| #11 | AP1 | ARP10 | UP REGULATED | Aminolevulinate (ALA) delta synthase Involved in heme biosynthetic pathway. |
| #12 | AP1 | ARP17 | UP REGULATED | IL-17, a pro inflammatory cytokine |
| #13 | AP1 | ARP17 | UP REGULATED | Heat shock protein DNAJ like Involved in stress and inflammation |
| #14 | AP1 | ARP18 | DOWN REGULATED | SATB1, a homeodomain protein acts as a transcription suppressor |

The remaining 5 are currently being sequenced and characterized. Genes 1, 2 and 5 have been positively identified by database comparisons. These are genes coding for proteins, not previously implicated in SEB action on lymphoid cells. They have varying activities and functions; there is a common theme of association with adhesion molecule function. These proteins may provide clues for new approaches in the treatment of lethal shock.

Although some gene sequences are not identified, the diagnosis of toxin can be made based on the location of the gene on the gel as shown in FIG. 37.

Discussion of the Genes in Table 1.

Gene #1—Connective tissue activating protein III (CTAP-III)

A cDNA which codes for a protein released from activated platelets and represents an inactive precursor connective tissue activating protein III (CTAP-III) (85 amino acids) was down regulated. This inactive precursor chemokine has shown to be proteolitically cleaved by leukocytes and leukocyte derived proteases at the N-terminus (Harter et al., 1994). These proteases have been shown to proteolitically process the above inactive chemokine to a neutrophil activating chemokine near sites of inflammation and vascular lesions (Harter, et al., 1994). The activation of the neutrophil activating chemokine has shown to aggravate the course of thrombotic diseases and their sequelae, as in atherosclerosis, by inducing inflammation and tissue damage (Walz, et al., J. Exp. Med. 170(5), 1745–1750, 1989). Inflammation and tissue damage are two conditions that are widely associated with SEB exposure. Here we show a cDNA, which had a high identity to CTAP-III, which was down-regulated through DD-PCR, and the down regulation was confirmed through RT-PCR and northern hybridization (FIG. 1). This cDNA has never been implicated with SEB activation and explains some of the conditions exposed by SEB exposure.

Gene #2—Chondroitin Sulphate Proteoglycan Versican 1

A cDNA that was down regulated is known to code for a chondroitin sulphate proteoglycan versican V1 that belongs to a growing family of large aggregating proteoglycans (Doege, et al., J. Biol. Chem, 266, 894–902, 1991; Doege, et al., J. Biol. Chem, 262, 17757–17767, 1987). The side chains containing a few chondroitin sulphate chains of these proteins protects the endothelium from oxidant injury and direct cytotoxycity (Nakazona, et al., Proc. Natl. Acad. Sci. USA, 88, 10045–10048, 1991; Abrahamsson, et al., Circ. Res., 70, 264–271 1992; Redni, et al., biochem. J., 252, 515–519, 1988). It is known that the changes in heparan sulfate metabolism might lead to profound changes in the physiology of blood vessels and removed from the endothelium in the course of inflammation. This was present in all types of blood vessels, ranging from the large caliber aorta to smallest capillaries. A decrease in proteoglycan may contribute to the loss of barrier properties therefore reducing in the thickness of the blood vessels, which may contribute to low blood pressure conditions, which is common in patients exposed to SEB and are symptoms associated with SEB induced shock. It is the first time such a gene has been identified to explain the low blood pressure conditions associated with SEB.

Gene #3

A novel gene that appeared on the gel but did not match with any of the available sequences of GenBank.

Gene #4—Interleukin-6 (IL-6)

Figure 5:
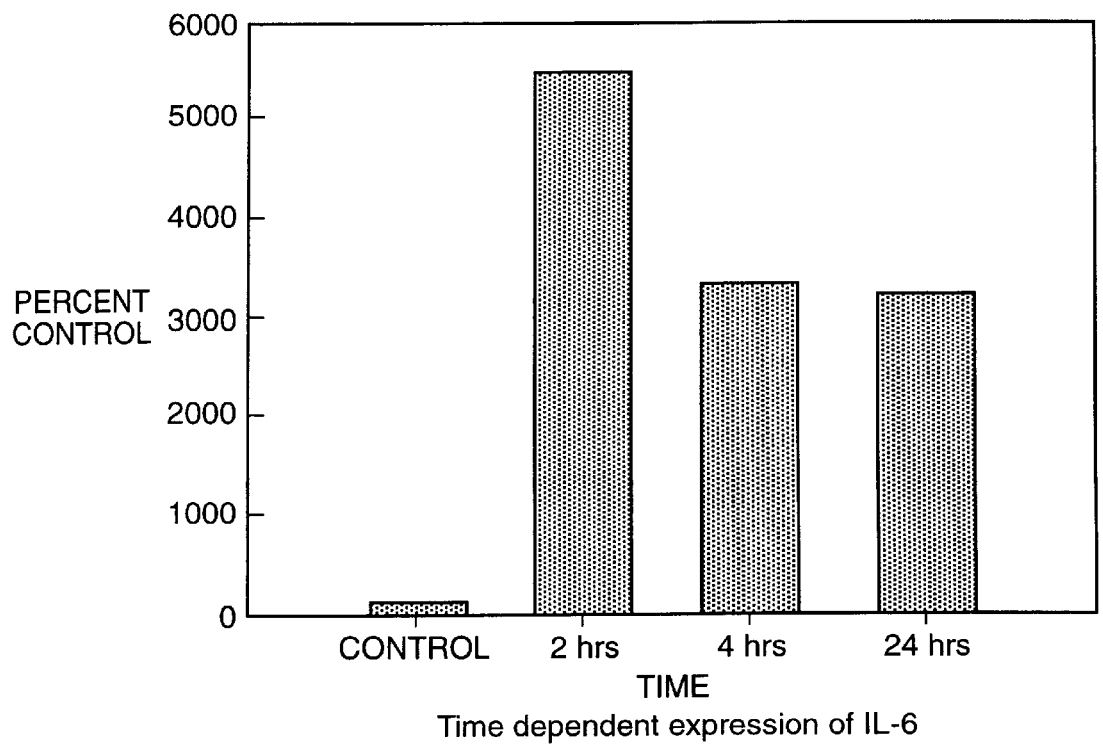
FIG. 5 is a graph showing a time dependent expression of IL-6.
Figure 6:
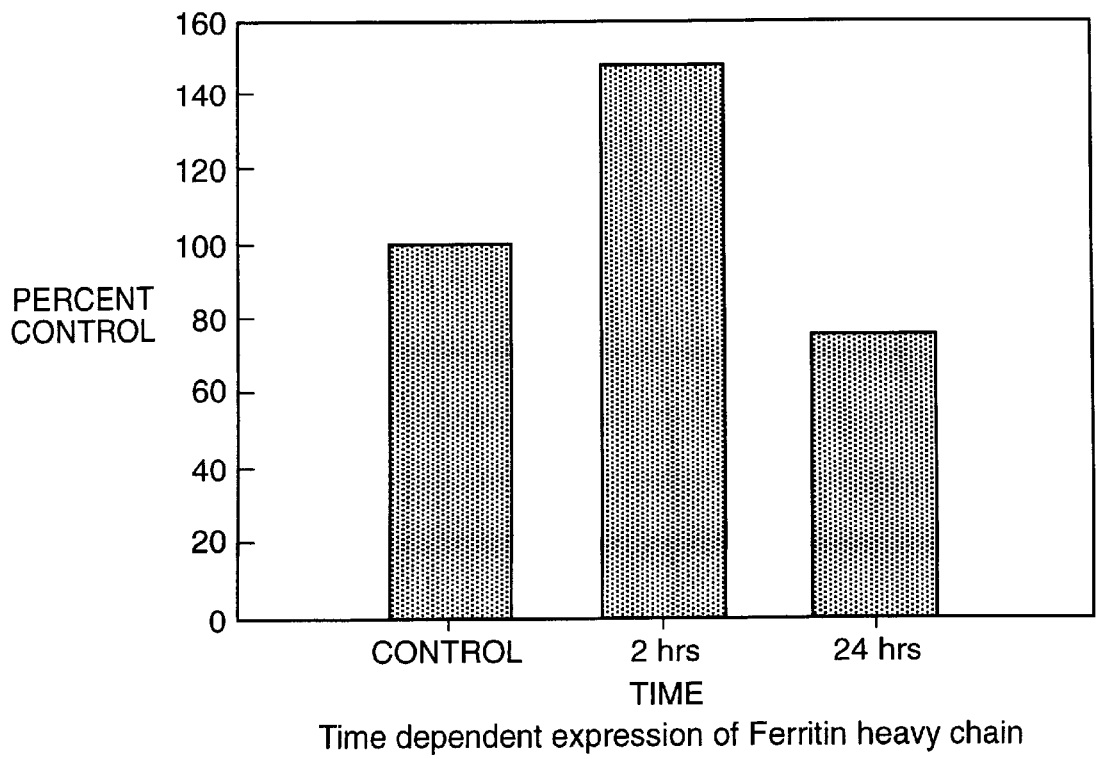
FIG. 6 is a graph showing a time dependent expression of Ferritin heavy chain.
Figure 7:
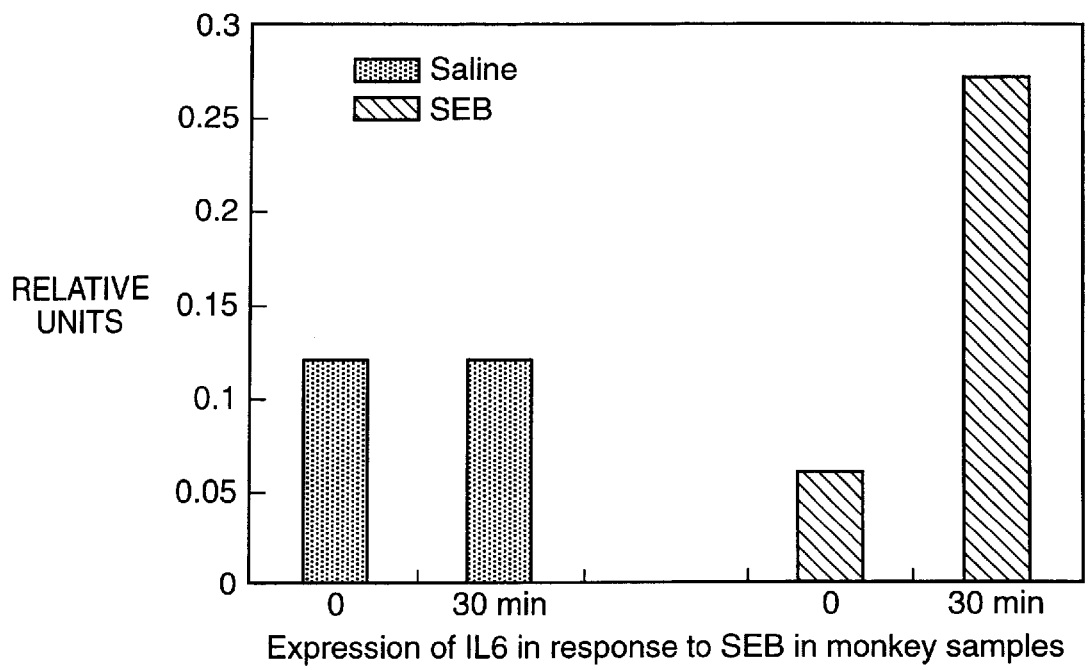
FIG. 7 is a graph showing a time dependent expression of IL-6 in response to SEB in monkey samples.
Figure 8:
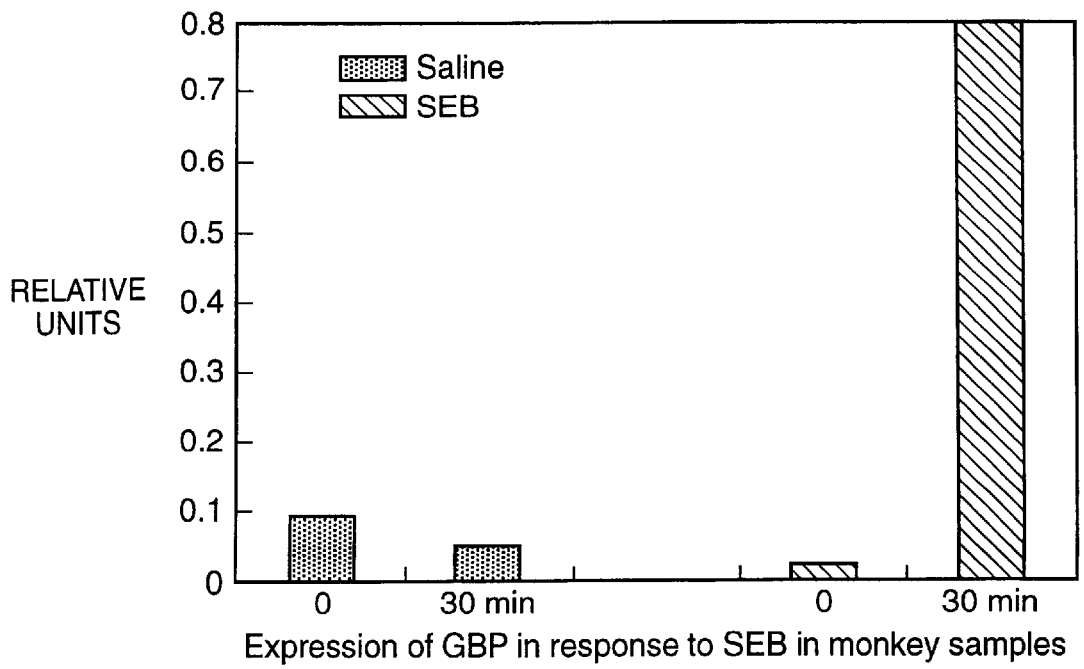
FIG. 8 is a graph showing a time dependent expression of GBP in response to SEB in monkey samples.
Figure 9:
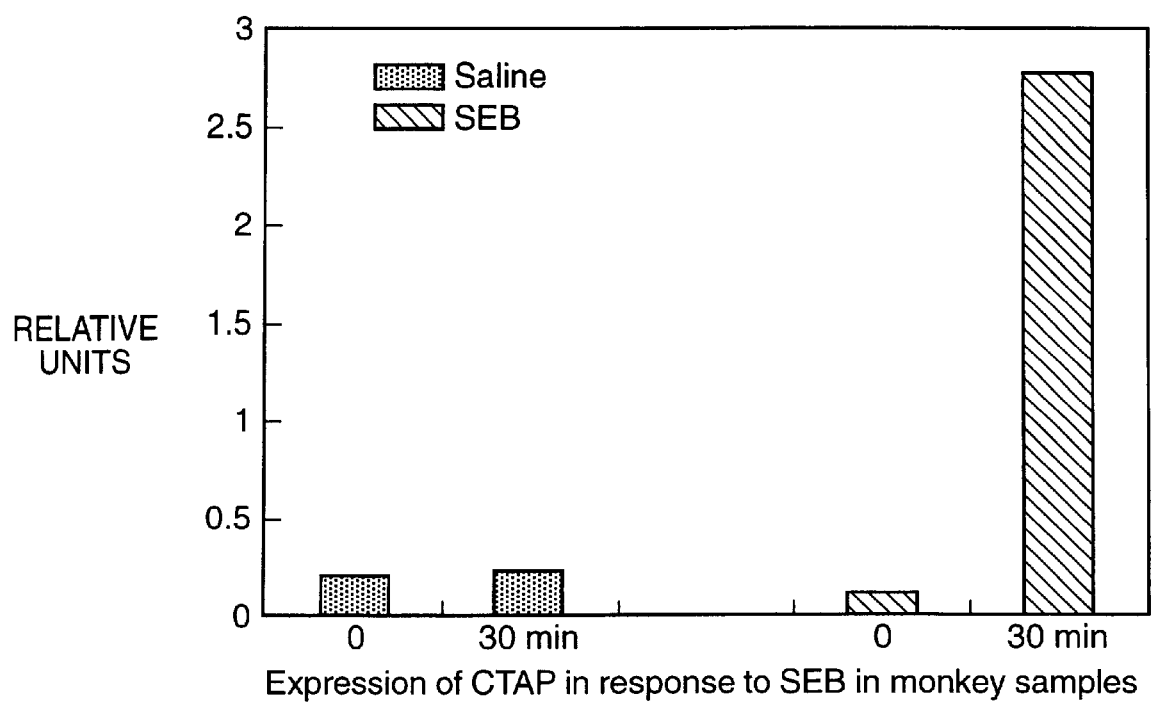
FIG. 9 is a graph showing a time dependent expression of CTAP in response to SEB in monkey samples.

Expressing of high levels of interleukin-6 by SEB is well documented. Experiments done on peripheral blood mononuclear cells (PBMC), with SEB have indicated the detection of elevated levels of IL-6 within 48 hours (Sperber, et al., Clin Degn Lab Immunol., 4, 473–477, 1995). Other experiments done using nonlethal dose SEB studies on human primates have indicated significant increased levels of IL-2 and IL-6 after four hours of receiving non lethal doses of SEB (Kerakaumer, et al., Mil. Med., 9, 612–615, 1997). Our results agreed with the above results, as we also observed high levels of IL-6 production within two hours of SEB induced human lymphoid cells first by DD-PCR and second by RT-PCR (FIG. 5). As IL-6 is a common cytokine induced by many toxins, it cannot be used to differentiate the effect of SEB from other toxins.

Gene #5—Myosin class 1 (Myc-1)

A cDNA, which coded for myosin class 1 was clearly up-regulated through DD-PCR. This motor domain containing proteins have shown to lead to significant cardiac dysfunction (Colbert, et al., J. Clin. Invest., 100, 1958–1968, 1997) showed a two fold up-regulation through RT-PCR and may explain the cardiac discomfort observed in subjects who are already suffering from other diseases and elderly who have been exposed to SEB.

Gene #6—Hypoxia inducible factor 1 (HIF-1)

Figure 4:
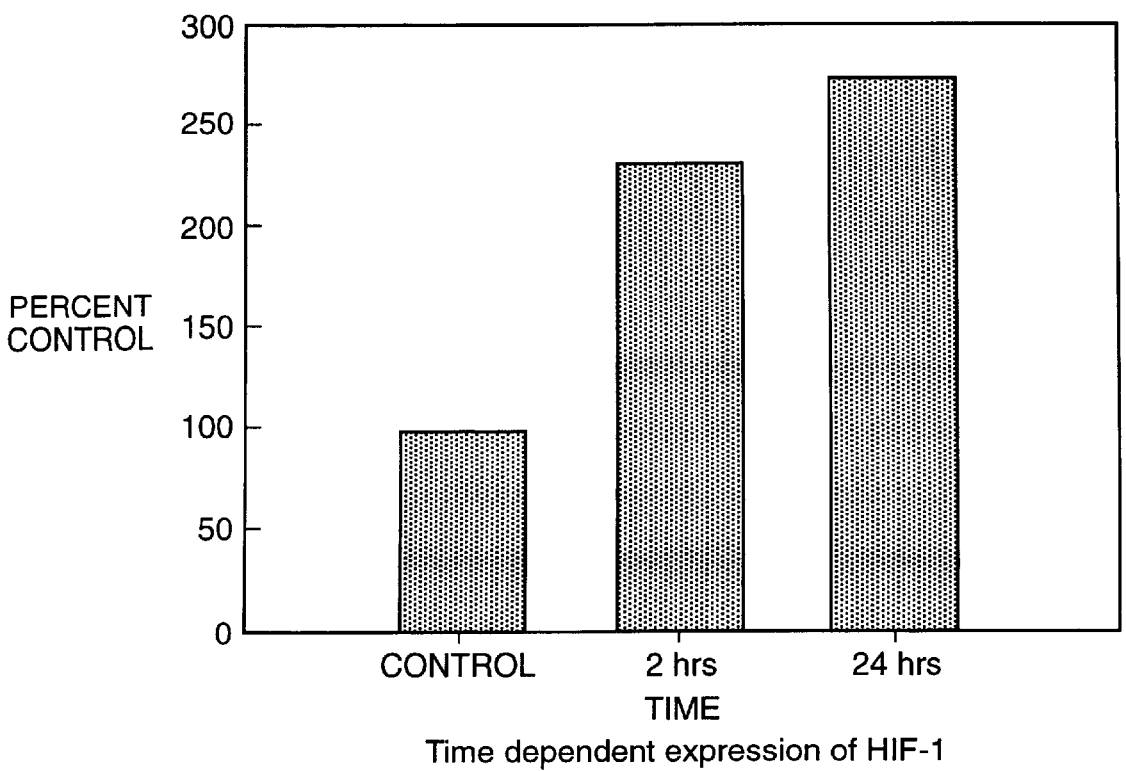
FIG. 4 is a graph showing a time dependent expression of HIF-1.

Upon stimulation by SEB a set of genes that are observed under reduced oxygen content were differentially expressed. A key step to hypoxia inducible activation is the formation of a heterodimeric complex of two helix loop helix PAS proteins (Wang, et al., Proc. Natl. Acad. Sci. USA, 92, 5510–5514, 1995). The helix loop helix transcriptional factor consists of a 120 kDa subunit complexed with a 90–94 kDa subunit induces respiratory distress. The up regulation of this cDNA, which codes for hypoxia inducible factor-1 (HIF-1) detected through DD-PCR was confirmed by RT-PCR (FIG. 4). The increase in cDNA expression of the helix loop helix transcriptional factor which encodes glycolytic enzymes and responsible for respiratory distress has never been implicated with SEB and clearly could directly be involved in respiratory problems due to its up regulation.

Gene #7, #9 and #10

Novel genes that appeared on the gels but did not match with any of the available sequences in Gen Bank.

Gene #8—Guanylate binding protein (GBP-1)

Figure 3:
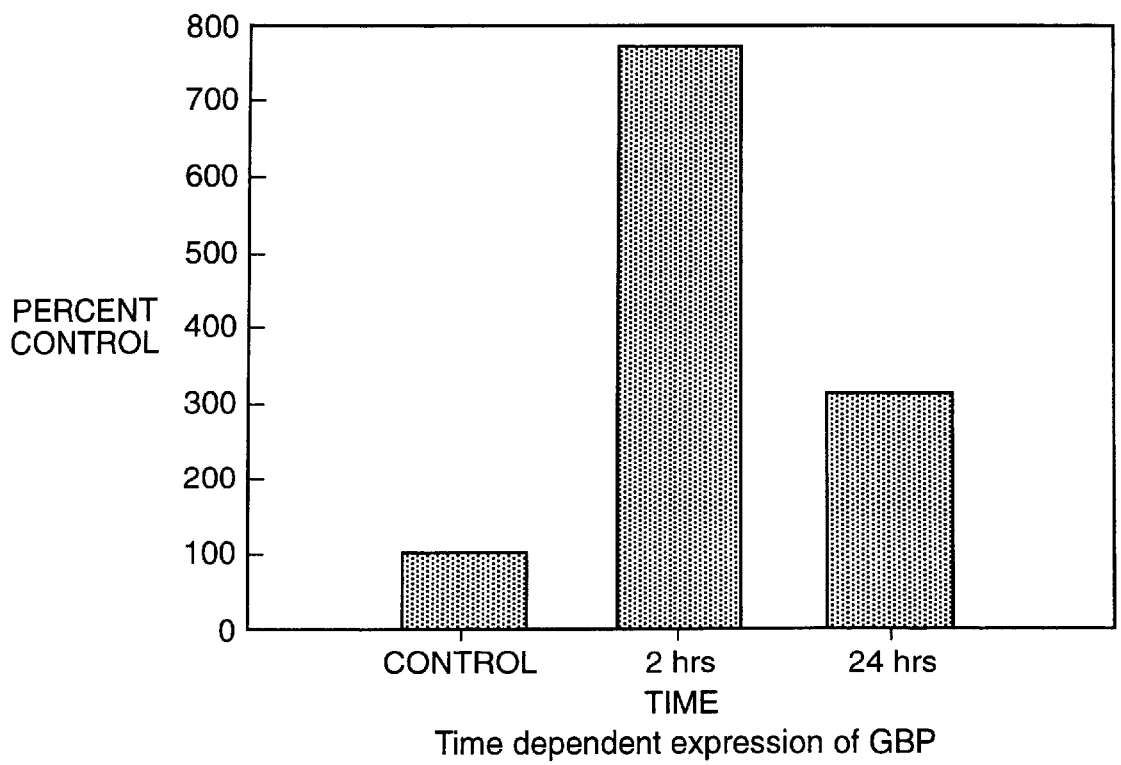
FIG. 3 is a graph showing a time dependent expression of GBP.

An up-regulated cDNA detected through DD-PCR is known to code for an interferon (IFN) induced 67 kDa guanylate binding protein-2, which has a wide variety of basic cellular functions such as protein synthesis, signal transduction, and intracellular protein transcription (Bourne, et al., Cell, 53, 669–671, 1988). Its ability to increase cyclase activity results in the production of high levels of NO, vasodilation and a threat to the endothelium. SEB induction of this gene suggests (FIG. 3) its role in producing high levels of cAMP by increasing cyclase activity as well vasodilation, which might in turn lead to lethal shock. This is a gene that not only has never been implicated with SEB but also is specific for this toxin.

Confirmation of Gene Changes in Monkey Samples

EXAMPLE 1

We exposed several monkeys with a sublethal dose of SEB and the controls with a saline challenge, isolated blood cells and prepared RNA from them. RT-PCR was performed for three separate genes that were altered in response to SEB in human lymphocytes. IL6 showed an increase over the control monkey samples suggesting that this cytokine does play a crucial role in SEB induced toxicity (FIG. 7). We further analyzed the levels of CTAP and GBP and found both the genes to be up regulated in 30 min after exposure to SEB (FIG. 8,9). This confirms the data we observed in vitro with human lymphoid cells. These genes can be thus be used as markers for exposure to SEB in a time dependent manner.

Differences in Responses in SEB and LPS Exposed Cells:

Comparison of Changes in Gene Expression in SEB and LPS Induced Lymphoid Cells:

When genes identified by DDPCR were analyzed and compared in two different toxins, we found there were some differences in their expression patterns (Table 2). As shown in FIGS. 10–13, four genes showed different expression patterns induced by SEB or LPS. This suggests that each toxin or BW agent will have a unique pattern of gene expression that is induced in the host. Table 3 further summarizes the total changes observed in lymphoid cells in response to these two toxins.

Gene Changes Observed in Human Kidney Cells:

Expression Pattern of RhoE in Human Lymphoid Cells

RhoE is a small G protein that lacks intrinsic GTPase activity (Foster, et al., 1996). This protein is involved in cell adhesion. As shown in FIG. 14 there is a distinct down regulation of this protein in kidney cells. This protein has been shown to block actin stress fiber formation which ultimately is known to induce apoptosis. The down regulation of this gene suggests that cell adhesion is lost in kidney cells which ultimately induces cell death.

Comparison of Gene Changes Induced by SEB and LPS in Kidney Cells:

Genes such as GBP, IL6 and Ferritin were induced by LPS in the kidney cells (FIGS. 15–18). Ferritin showed a time dependent decrease in expression in response to LPS (FIGS. 17*a,b*). Changes in IL6 occurred much later after 24 hrs of exposure to the toxin however there was no change observed by SEB in these cells. In contrast SEB induced a dramatic change in lymphoid cells by 2 hrs of exposure whereas LPS showed no change in these cells. Genes encoding HIF-1 and Myosin heavy chain were both up regulated in kidney cells but LPS did not show any change (FIGS. 19, 20). We also observed that Superoxide dismutase was also stimulated in response to SEB (data not shown).

METHODS OR PROCEDURES

Primary Cell Cultures: Cell Isolation/Purification from Plasma of Healthy Human Donors.

Human lymphocytes and monocytes were prepared from leukopaclcs from normal donors according to Jett et al 1994 using lymphocyte separation medium histopaque 1077. Lymphocytes and monocytes were purified and separated further by count:erflow centrifugation-elutriation with PBS as the eluant.

Differential Display:

The differential display approach was introduced in the past few years and has become a potent tool for identifying genes that are differentially expressed in various eukaryotic cells and organs or under altered conditions.

The cells were treated for various time periods (1 hr–24 hrs) with these toxins and mRNA was isolated. The technique of differential display involves isolation of undegraded MRNA free of genomic DNA. Reverse transcriptase (RT) is necessary for conversion of mRNA to single stranded cDNA by using a two base-anchored oligo-dT primer T12MA, T12MC, T12MG and T12MT where M is a mixture of dA, dC and dG obtained from Beckman Coulter, Calif. A fraction of this reaction mixture of the cDNA was amplified by PCR using appropriate primers and radiolabeled dNTP. The PCR products were separated on a 6% Sequencing polyacrylamide gel, after developing the gel we looked for differences in the treated vs untreated lanes for presence/absence/intensity of bands. Both positive and negative controls were included to avoid false positives. Once the different bands are identified, they were cut out o f the gel, eluted and reamplified by PCR using the same primers to confirm the changes. The final confirmation was carried out on a Northern blot, where the mRNA samples were run on a gel and each of these bands labeled and used as a probe to see if the changes are reproducible. Once this is confirmed then the cDNAs was cloned into a vector and sequenced to identify the nature of the gene. The sequence was compared to the gene bank database to look for homology with other already identified genes or find out if they are unique in any way. RT-PCR was also performed to confirm the changes in gene expression by each agent.

This technique is highly sensitive and reproducible, and is a rapid method for identifying unique genes, quantitatively, which are altered upon treatment of cells with the compound of interest. This information provides a library of genes that are activated by toxins/agents producing serious illness, it will aid in identification of new treatment modalities. Thus this technique has enormous potential; identifying the changes occurring at the molecular level in a system has radically changed concepts in biomedical research by opening new avenues for diagnosis and therapy. We have already used this technique and have identified 15 genes altered in expression in our prototype studies with SEB, as will be discussed later.

Other techniques that can be used to identify the genes induced by toxins are Serial Analysis of Gene Expression (SAGE) and a Gene Array technique to identify the changes induced by these toxic agents.

Using these techniques, one can screen 20,000 genes at a time which will yield information in a time efficient manner and which can quickly build a gene library for each toxic agent.

Measurement of Gene Changes by Using DNA Chips:

This is an innovative approach of analyzing changes in gene expression in a sample for a large number of genes simultaneously. The development of recent technologies allows to immobilize DNA to a solid surface such as glass and exposed to a set of labeled probes; or an array of oligonucleotide probes are synthesized followed by on-chip mobilization or on another substrate such as nitrocellulose filters. The array is then exposed to labeled sample DNA, hybridized and the positive signals analyzed.

Arrays of allele-specific oligodeoxynucleotides covalently attached to microscope glass slide through spacer linkers are used. Forty-eight oligonucleotides in duplicates can be attached to glass microscope slides in an area of 2.5 cm by 0.75 cm with the use of a high speed arraying machine. Because allele-specific oligonucleotide probes for each mRNA are specifically chosen and synthesized in known locations on the arrays, the hybridization patterns and intensities can be interpreted in terms of the identity and the concentrations of various mRNAs simultaneously. Multiple oligonucleotides for each cDNA can be used to better quantify the concentration of mRNA. Probes specific for each symptoms will be used such as genes for lethal shock, or genes for neurotoxic agents that will determine which agent was involved in causing the gene changes in the blood sample.

EXAMPLE 2

In this example, lymphoid cells are treated with pathogens/toxins: 2, 6, 16 hr exposure; RNA is isolated. Lymphoid cells are exposed to various BW agents for defined time periods and RNA free of genomic DNA is isolated using trizol method. Enough human lymphoid cells are started to isolate RNA at all the time points for each BW agent. This RNA is used for screening of changes in gene expression pattern by several methods.

EXAMPLE 3

In this example, DD-PCR, +/−SAGE or Gene Array is used to isolate altered genes, purify, amplify. DD-PCR is performed using various combinations of anchored and arbitary primers to cover the entire CDNA population. The DD-PCR products are resolved on a sequencing gel and changes for each agent analyzed. At each step proper negative and positive controls are used and samples are handled in duplicates to avoid false signals. Genes are up- or down-regulated by each BW agent. Gene arrays from Genome Systems Inc. St. Louis, Mo., can be used to screen a whole library of 18,000 genes at a given time. To obtain more global changes SAGE can be used, a new technique for analyzing the whole cDNA more rapidly.

The techniques outlined in the Examples above are used to identify specific genes altered in response to the 6 listed BW agents. We have also verified the changes using dose and time course variations in direct analysis using standard PCR primers. Changes identified from all these techniques can be verified by northern blots to avoid false positives. Some of the BW agents used may require the longer (24 h) incubation times for gene changes to appear; also, secondary effects (because of other tissues being the BW target) may cause gene changes which would not be seen in the in vitro system. Potentially, some of those changes will still be picked up upon in vivo exposure to the BW agent.

EXAMPLE 4

Purify, sequence genes from Example 3, identify using GENBANK databases; catalogue the genes identified for each specific agent and select genes which will discriminate among a variety of B/W agents. Each gene is re-amplified and sequenced using either cycle sequencing kit (Amersham) or using the ABI kit. We have currently found that $2/3$ of the genes give a positive match in the Genebank database. Any new genes that look important as a BW agent marker, are cloned into a bacterial plasmid; we can then screen a cDNA library and identify the gene. This will provide a selected a pattern or panel of genes for each BW agent.

EXAMPLE 5

After confirming the changes identified by DDPCR, SAGE and Gene array, specific oligos can be designed that will be used to verify responses to various agents in vitro and in vivo. These genes can be attached to a matrix (membrane or on glass surfaIce) for establishing a diagnostic tool for rapid detection.

EXAMPLE 6

RT-PCR and northern analyses to confirm these changes, and determine alterations at intermediate time periods. Develop a quantitative PCR for selected genes: Specific primers are designed for each gene identified and a northern blot analysis is performed for all the RNA samples. A standardize method is used to quantify our PCR results using nonradioactive probes. All necessary controls are used for such a procedure.

EXAMPLE 7

Expose animals/non-human primates to the BW agent in question: Blood samples are taken from various animals exposed to respective BW agents at 0, 2, 16 h; the blood samples are collected, lymphoid cell fraction are isolated, RNA is extracted, quantitative PCR measurements based on the unique genes altered in response to each specific agent are performed. The selected genes will be confirmed by simple RT-PCR methods, then if appropriate these samples will be tested on DNA array matrices.

TABLE 1

Changes in Gene Expression Identified in Lymphoid Cells Treated with SEB*

| GENE | PRIMERS Anchored | Arbitrary | CHANGES IN EXPRESSION | FUNCTION |
|---|---|---|---|---|
| #1 | AP3 | ARP3 | DOWN REGULATED | CTAP-III (gb MS4995), Involved in early stages of wound healing; has heparanase-like enzyme activity. |
| #2 | AP3 | ARP4 | DOWN REGULATED | Proteoglycan $V_1$ (EMB X15998), An adhesion molecule, which regulates vascular smooth muscle tone and is involved in lymphoid cell proliferation. |
| #3 | AP1 | ARP2 | UP REGULATED | A NOVEL GENE, No matching sequence have been found in either GENBANK and EMBL databases. |
| #4 | AP1 | ARP2 | UP REGULATED | IL-6 (gb M29150), A cytokine involved in inflammation, T-cell proliferation and release of cascades of other mediators |
| #5 | AP3 | ARP3 | UP REGULATED | Myosin 1 (emb AJ0013811), A contractile protein which has been characterized as contributing to cardiomyopathy; A regulator of motor activity. |
| #6 | AP3 | ARP3 | UP REGULATED | HIF-1 (gb AF050127), A protein which contributes to respiratory distress |
| #7 | AP3 | ARP4 | DOWN REGULATED | Currently no positive match with gene database |
| #8 | AP3 | ARP2 | UP REGULATED | Guanylate binding protein-2 (gb M5542), A protein which regulates cyclase activation |
| #9 | AP1 | ARP2 | UP REGULATED | Currently no positive match with gene database |
| #10 | AP3 | ARP2 | UP REGULATED | Currently no positive match with gene database |
| #11 | AP1 | ARP10 | UP REGULATED | Aminolevulinate (ALA) delta synthase Involved in heme biosynthetic pathway. |
| #12 | AP1 | ARP17 | UP REGULATED | IL-17, a pro inflammatory cytokine |
| #13 | AP1 | ARP17 | UP REGULATED | Heat shock protein DNAJ like Involved in stress and inflammation |
| #14 | AP1 | ARP18 | DOWN REGULATED | SATB1, a homeodomain protein acts as a transcription suppressor |

TABLE 2

| KNOWN GENES SPECIFIC FOR SEB | | |
|---|---|---|
| 1. 5-LO | up regulated | 5 fold |
| 2. GBP | up regulated | 3 fold |
| 3. p-Glycoprotein | up regulated | 7 fold |
| KNOWN GENES SPECIFIC FOR LPS | | |
| 1. NADH | down regulated | 20 fold |
| NOVEL GENES INDUCED BY SEB | | |
| 1. AP8/ARP3 | up regulated | 51 fold |
| 2. AP1/ARP2 | up regulated | 51 fold |
| 3. AP3/ARP3 | down regulated | 2 fold |
| 4. AP1/ARP2 | up regulated | 13 fold |
| UNKNOWN GENES INDUCED BY LPS | | |
| 1. AP1/ARP2 | down regulated | 9–10 fold |
| 2. AP3/ARP3 | down regulated | 4–6 fold |

TABLE 3

COMPARISON OF EFFECTS OF SEB AND LPS ON A SET OF DIFFERENTIALLY EXPRESSED GENES

| | SEB (100 ng/ml) | | LPS (100 ng/ml) | |
|---|---|---|---|---|
| IDENTITY OF GENE | 4 hrs/ change fold | 24 hrs/ change fold | 4 hrs/ change fold | 24 hrs/ change fold |
| 5-LO | UP/1.5 | UP/3 | X | X |
| IL-6 | UP/32 | UP/30 | UP/11 | UP/10 |
| PROTEOGLY CAN $V_1$ | DOWN/0.8–0.5 | DOWN/0.55 | N.D | N.D |
| CTAP-III | DOWN/ 0.40 | DOWN/0.50 | DOWN/0.3–0.4 | DOWN/0.3 |
| GBP-2 | UP/7–3.5 | UP/3.2 | X | X |

TABLE 3-continued

COMPARISON OF EFFECTS OF SEB AND LPS ON A SET OF DIFFERENTIALLY EXPRESSED GENES

| | SEB (100 ng/ml) | | LPS (100 ng/ml) | |
|---|---|---|---|---|
| IDENTITY OF GENE | 4 hrs/ change fold | 24 hrs/ change fold | 4 hrs/ change fold | 24 hrs/ change fold |
| FERRITIN HEAVY CHAIN | UP/1.4–0.8 | DOWN/0.8 | N.D | N.D |
| HIF-1 | UP/2.2–2.7 | UP/2.7 | DOWN/0.4 TO +1.3 | UP/1.3 |

Excised cDNA of differentially expressed genes by SEB were subjected to RT-PCR using custom designed primers.
Equal quantities of expressed DNA were resolved on an agarose gel, quantified, normalized with actin and the expression was compared to control levels.
X represents no effect,
'up' and 'down' represents an up and down regulation of the gene by the respective toxin respectively and
N.D represents the values not obtained at the respective time point.

TABLE 4

SEB-INDUCED DIFFERENTIAL GENE EXPRESSION IN PTKC

| | AP*1 | AP2 | AP3 | AP4 |
|---|---|---|---|---|
| ARP*1 | 1 up regulated | | 2 up regulated | 3 down regulated |
| ARP2 | 1 up regulated 1 down regulated | | 3 down regulated | |
| ARP3 | 2 up regulated 1 identified | 2 down regulated | | 4 up regulated |
| ARP4 | 1 up regulated | | 4 down regulated 1 identified | 2 down regulated |
| ARP5 | 3 up regulated 1 down regulated | | 2 down regulated | |
| ARP6 | | | | |

Renal proximal tubule epithelial cells were incubated with or without 50 ng/ml SEB for 12 hours.
Total mRNA was isolated and DD-PCR performed as described.
The 32 differentially expressed genes are currently at various stages of isolation, purification, sequencing, and identification.
*AP—anchored primer
**ARP—arbitrary primer
14 up regulated
18 down regulated

TABLE 5a

Changes in Gene Expression Identified in Lymphoid Cells Treated with Anthrax*

| GENE | PRIMERS Anchored | Arbitrary | CHANGES IN EXPRESSION | FUNCTION |
|---|---|---|---|---|
| #1 | AP2 | ARP1 | DOWN REGULATED | HCI-Human Collagenase Inhibitor Involved in tissue remodeling, blocks the activities of metalloproteinases |
| #2 | AP1 | ARP3 | DOWN REGULATED | EIF-3 Eukaryotic translation initiation factor-3 |
| #3 | AP2 | ARP1 | UP REGULATED | A NOVEL GENE. No matching sequence have been found in either GENBANK and EMBL databases. |
| #4 | AP2 | ARP1 | UP REGULATED | ILT-6 immunoglobulin like transcripts Expressed in immune cells, acts as cell surface receptors similar to NK cell receptors |
| #5 | AP1 | ARP18 | UP REGULATED | Cathepsin-L, a lysosomal enzyme involved in |
| #6 | AP1 | ARP18 | UP REGULATED | Long chain acyl CoA synthetase |

TABLE 5a-continued

Changes in Gene Expression Identified in Lymphoid Cells Treated with Anthrax*

| GENE | PRIMERS | | CHANGES IN EXPRESSION | FUNCTION |
|---|---|---|---|---|
| | Anchored | Arbitrary | | |
| #7 | AP2 | ARP18 | DOWN REGULATED | Currently no positive match with gene database |
| #8 | AP1 | ARP18 | DOWN REGULATED | FGF-13 |
| #9 | AP1 | ARP18 | UP REGULATED | Currently no positive match with gene database |
| #10 | AP1 | ARP18 | UP REGULATED | Currently no positive match with gene database |

*Total of 85 bands have been identified to be altered by Anthrax in human lymphocytes using differential display. So far 10 bands have been sequenced, the rest are being sequenced currently.

TABLE 5b

Status of Anthrax Bands (85 genes)
STATUS OF ANTHRAX BANDS

| Notebook | Pages | Band # | Expression | Status |
|---|---|---|---|---|
| 2 | 158–168 | 1 | up | Needs to be cloned |
| 2 | 158–168 | 2 | up | Needs to be cloned |
| 2 | 158–168 | 3 | up | Needs to be cloned |
| 2 | 158–168 | 4 | up | Needs to be cloned |
| 2 | 158–168 | 5 | up | re-sequence, couldn't read last gel run |
| 2 | 158–168 | 6 | up | Needs to be cloned |
| 2 | 158–168 | 7 | up | Needs to be cloned |
| 2 | 158–168 | 8 | up | Needs to be cloned |
| 2 | 158–168 | 9 | up | Needs to be cloned |
| 2 | 158–168 | 10 | up | re-sequence, couldn't read last gel run |
| 2 | 158–168 | 11 | up | Needs to be cloned |
| 2 | 158–168 | 12 | up | re-sequence, couldn't read last gel run (run sequencing rxn again and gel) |
| 2 | 158–168 | 13 | up | Needs to be cloned |
| 2 | 158–183 | 14 | up | Gene identified: Human collagenase inhibitor mRNA (p168); primers designed, "HCI" (p178); have already run RT-PCR w/anthrax from human lymphs from 0–24 hrs; Next step: RT-PCR with animal lymphs |
| 2 | 158–168 | 15 | down | Needs to be cloned |
| 2 | 158–168 | 16 | up | Needs to be cloned |
| 2 | 158–183 | 17 | down | Gene identified: Homo sapiens eukaryotic translation initiation factor 3 (p174); primers designed, "EIA" (p178); have already run RT-PCR w/anthrax from human lymphs from 0–24 hrs; Next step: RT-PCR with animal lymphs |
| 2 | 158–168 | 18 | down | re-sequence, couldn't read last gel run (run sequencing rxn again and gel) |
| 2 | 158–168 | 19 | down | Needs to be cloned |
| 3 | 18,20,32–37 | 20 | down | p32, cold reamp gel shows multiple bands; Next step: clone sequence |
| 3 | 18,20,32–37 | 21 | down | BLAST search results show several possible matches; further research this sequence (see folder "BLAST Search Results"); Next Step: re-clone |
| 3 | 18,27–8 | 22 | up | No apparent bands present after several repeated hot/cold reamps; possibly no template???; Next step: try to clone from originial band |
| 3 | 18,27–8 | 23 | down | No apparent bands present after several repeated hot/cold reamps; possibly no template???; Next step: try to clone from originial band |
| 3 | 18,27–8 | 24 | down | No apparent bands present after several repeated hot/cold reamps; possibly no template???; Next step: try to clone from originial band |
| 3 | 18,20,32–37 | 25 | down | BLAST search results show several possible matches; further research this sequence (see folder "BLAST Search Results"); Next Step: re-clone |
| 3 | 18,20,32–37 | 26 | up | Gene identified: Homo sapien mRNA for long-chain acyl-CoA synthetase (p35); primers designed, "ACOA" (p37); Next step: run RT-PCR with anthrax RNA at different time points |
| 3 | 18,27–8 | 27 | down | No apparent bands present after several repeated hot/cold reamps; possibly no template???; Next step: try to clone from originial band |
| 3 | 18,20,32–37 | 28 | down | BLAST search results show several possible matches; further research this sequence (see folder "BLAST Search Results"); Next Step: re-clone |
| 3 | 18,27–8 | 29 | down | No apparent bands present after several repeated hot/cold reamps; possibly no template???; Next step: try to clone from originial band |
| 3 | 18,20,32–37 | 30 | down | BLAST search results show several possible matches; further research this sequence (see folder "BLAST Search Results"); Next Step: re-clone |
| 3 | 18,20,32–37 | 31 | down | BLAST search results show several possible matches; further research this sequence (see folder "BLAST Search Results"); Next Step: re-clone |
| 3 | 18,20,32–37 | 32 | down | BLAST search results show several possible matches; further research this sequence (see folder "BLAST Search Results"); Next Step: re-clone |
| 3 | 18,20,32–37 | 33 | down | Gene identified: Fibroblast Growth Factor 13 (p36); primers designed, "FGF13" (p37); Next step: run RT-PCR with anthrax RNA at different time points |
| 3 | 18,27–8 | 34 | up | No apparent bands present after several repeated hot/cold reamps; possibly no template???; Next step: try to clone from originial band |
| 3 | 18,27–8 | 35 | down | No apparent bands present after several repeated hot/cold reamps; possibly no template???; Next step: try to clone from originial band |

TABLE 5b-continued

Status of Anthrax Bands (85 genes)
STATUS OF ANTHRAX BANDS

| Note-book | Pages | Band # | Expression | Status |
|---|---|---|---|---|
| 3 | 18,27–8 | 36 | down | No apparent bands present after several repeated hot/cold reamps; possibly no template???; Next step: try to clone from originial band |
| 3 | 18,27–8 | 37 | down | No apparent bands present after several repeated hot/cold reamps; possibly no template???; Next step: try to clone from originial band |
| 3 | 18,20,32–37 | 38 | down | BLAST search results show several possible matches; further

TABLE 6

Changes in Gene Expression Identified in Lymphoid Cells Treated with *Yersinia pestis*

| GENE | PRIMERS Anchored | Arbitrary | CHANGES IN EXPRESSION | FUNCTION |
|---|---|---|---|---|
| #1 | AP1 | ARP2 | DOWN REGULATED | To be sequenced |
| #2 | AP1 | ARP1 | DOWN REGULATED | To be sequenced |
| #3 | AP1 | ARP2 | UP REGULATED | To be sequenced |
| #4 | AP1 | ARP2 | UP REGULATED | To be sequenced |
| #5 | AP3 | ARP1 | UP REGULATED | To be sequenced |
| #6 | AP3 | ARP1 | UP REGULATED | To be sequenced |
| #7 | AP1 | ARP2 | UP REGULATED | To be sequenced |
| #8 | AP1 | ARP2 | UP REGULATED | To be sequenced |
| #8 | AP1 | ARP2 | UP REGULATED | To be sequenced |
| #9 | AP1 | ARP2 | UP REGULATED | To be sequenced |
| #10 | AP3 | ARP2 | UP REGULATED | To be sequenced |
| #11 | AP3 | ARP2 | UP REGULATED | To be sequenced |
| #12 | AP1 | ARP1 | UP REGULATED | To be sequenced |
| #13 | AP1 | ARP1 | UP REGULATED | To be sequenced |
| #14 | AP1 | ARP2 | DOWN REGULATED | To be sequenced |
| #15 | AP1 | ARP2 | DOWN REGULATED | To be sequenced |
| #16 | AP3 | ARP1 | DOWN REGULATED | To be sequenced |

*Total of 28 bands have been identified to be altered by Plague in human lymphocytes using differential display. They are in the process of being sequenced currently.

TABLE 7

Changes in Gene Expression Identified in Lymphoid Cells Treated with Cholera Toxin

| GENE | PRIMERS Anchored | Arbitrary | CHANGES IN EXPRESSION | FUNCTION |
|---|---|---|---|---|
| #1 | AP2 | ARP1 | UP REGULATED | Human T-cell surface antigen T11 (CD2) |
| #2 | AP4 | ARP1 | UP REGULATED | To be sequenced |
| #3 | AP1 | ARP3 | UP REGULATED | Cu/Zn Superoxide Dismutase (SOD) |
| #4 | AP2 | ARP2 | UP REGULATED | HOMO SAPIENS CLONE 24653 mRNA SEQUENCE |
| #5 | AP5 | ARP4 | UP REGULATED | TO BE SEQUENCED |
| #6 | AP5 | ARP4 | UP REGULATED | TO BE SEQUENCED |
| #7 | AP5 | ARP2 | UP REGULATED | TO BE SEQUENCED |
| #7 | AP5 | ARP3 | UP REGULATED | TO BE SEQUENCED |
| #8 | AP5 | ARP3 | UP REGULATED | TO BE SEQUENCED |
| #9 | AP5 | ARP3 | UP REGULATED | TO BE SEQUENCED |
| #10 | AP4 | ARP3 | UP REGULATED | TO BE SEQUENCED |
| #11 | AP4 | ARP2 | DOWN | TO BE SEQUENCED |
| #12 | AP4 | ARP2 | UP REGULATED | TO BE SEQUENCED |
| #13 | AP4 | ARP2 | UP REGULATED | TO BE SEQUENCED |
| #14 | AP4 | ARP2 | DOWN | TO BE SEQUENCED |
| #15 | AP4 | ARP2 | DOWN | TO BE SEQUENCED |
| #16 | AP4 | ARP2 | DOWN | TO BE SEQUENCED |
| #17 | AP4 | ARP1 | UP REGULATED | TO BE SEQUENCED |
| #18 | AP4 | ARP1 | UP REGULATED | TO BE SEQUENCED |

Total 32 genes have been isolated. They are being sequenced for identification.

While the preferred embodiments of the invention have been illustrated and described, it will be appreciated that various changes can be made therein without departing from the spirit and scope of the invention.

What is claimed is:

1. A method of pre-symptom diagnosis of exposure to a toxic agent comprising:
   obtaining a sample of mammalian body fluid or tissue from a subject;
   detecting a pattern of gene expression or protein expression present in said sample;
   comparing the pattern of gene or protein expression from said sample with a library of known patterns of gene or protein expressions for toxic agents; and
   determining whether the subject has been exposed to a toxic agent in said library and if said subject has been exposed to a toxic agent in said library, identifying said toxic agent based on information in said library.

2. The method of claim 1, wherein said sample comprises peripheral blood lymphoid cells.

3. The method of claim 1, wherein said sample comprises mammalian tissue.

4. The method of claim 1, wherein said toxic agent is LPS (lipopolysaccharide).

5. The method of claim 1, wherein said toxic agent is SEB (staphyloccocal enterotoxin B).

6. The method of claim 1, wherein said toxic agent is anthrax.

7. The method of claim 1, wherein said toxic agent is chorera.

8. The method of claim 1, wherein said toxic agent is Brucella.

9. The method of claim 1, wherein said toxic agent is plague.

10. The method of claim 1, wherein said toxic agent is botulinum toxin.

11. The method of claim 1, wherein said library comprises gene and protein patterns for SEB (staphyloccocal enterotoxin B), LPS (lipopolysaccharide), anthrax, cholera, Brucella, plague and botulinum toxin.

12. A method of diagnosing exposure to a toxic agent comprising the steps of:
   detecting an amount of protein or gene expression present in a sample of mammalian tissue or mammalian body fluids that has been unexposed to the toxic agent;
   detecting an amount of protein or gene expression present in a sample of mammalian tissue or mammalian body fluids that has been exposed to the toxic agent;
   determining the difference in the detected amount of protein/gene expression between the exposed and unexposed samples;
   comparing the difference to a library of expected protein/gene expression for predetermined toxic agents;

evaluating whether the difference indicates that said sample has been exposed to a particular toxic agent.

13. The method of claim 12, further comprising a step of identifying said toxic agent.

14. The method of claim 12, wherein said library of toxic agents comprises expected protein or gene expression for toxic agents selected from the group consisting of SEB (staphyloccocal enterotoxin B), LPS (lipopolysaccharide, anthrax, Brucella, plague, botulinum toxin, and cholera toxin.

15. The method of claim 12, wherein said expression is a gene expression.

16. The method of claim 12, wherein said expression is a protein expression.

17. The method of claim 1, wherein said toxic agent is a known toxic agent.

18. A method of pre-symptom diagnosis of exposure to a toxic agent, wherein said toxic agent is SEB (staphyloccocal enterotoxin), Anthrax, Cholera, LPS (lipopolysaccharide), or Plague comprising:

obtaining a sample of mammalian body fluid or tissue from a subject;

detecting a pattern of gene expression or protein expression present in said sample;

comparing the pattern of gene or protein expression from said sample with a library of known patterns of gene or protein expressions for toxic agents; and determining whether the subject has been exposed to said toxic agent and if said subject has been exposed to a toxic agent, identifying said toxic agent based on information in said library.

19. The method of claim 18, wherein said sample comprises lymphoid cells or kidney cells.

20. The method of claim 18, wherein said detecting is by DD-PCR (differential display-polymerase chain reaction), Gene Array and/or SAGE (serial analysis of gene expression).

* * * * *